United States Patent [19]
Yabe et al.

[11] Patent Number: 5,695,450
[45] Date of Patent: Dec. 9, 1997

[54] COVER-TYPE ENDOSCOPE APPARATUS

[75] Inventors: Hisao Yabe, Hachioji; Yoshihiro Iida, Tama; Akira Suzuki; Hideo Itoh, both of Hachioji; Yoshio Tashiro, Hino; Minoru Yamazaki; Osamu Tamada, both of Hachioji, all of Japan

[73] Assignee: Olympus Optical Co., Ltd., Tokyo, Japan

[21] Appl. No.: 38,657

[22] Filed: Mar. 29, 1993

[30] Foreign Application Priority Data

| Mar. 5, 1993 | [JP] | Japan | 5-009173 U |
| Mar. 5, 1993 | [JP] | Japan | 5-009174 U |
| Mar. 5, 1993 | [JP] | Japan | 5-009175 U |

[51] Int. Cl.⁶ ........................................ A61B 1/04
[52] U.S. Cl. .................. 600/123; 600/121; 600/153; 600/156
[58] Field of Search ................. 128/4, 6, 7, 844; 600/121, 123, 153, 156, 154, 155, 203, 187

[56] References Cited

U.S. PATENT DOCUMENTS

| Re. 34,110 | 10/1992 | Opie . | |
| 3,162,190 | 12/1964 | Del Gizzo . | |
| 4,245,624 | 1/1981 | Komiya | 600/153 X |
| 4,646,722 | 3/1987 | Silverstein | 128/4 |
| 4,721,097 | 1/1988 | D'Amelio | 128/4 |
| 4,741,326 | 5/1988 | Sidall | 128/4 |
| 4,825,850 | 5/1989 | Opie | 128/4 |
| 4,869,238 | 9/1989 | Opie | 128/6 |
| 4,886,049 | 12/1989 | Darras | 128/4 |
| 4,907,395 | 3/1990 | Opie | 53/434 |
| 4,991,564 | 2/1991 | Takahashi | 128/4 |
| 4,991,565 | 2/1991 | Takahashi | 128/4 |
| 4,997,084 | 3/1991 | Opie | 206/364 |
| 5,050,585 | 9/1991 | Takahashi | 128/4 |
| 5,058,567 | 10/1991 | Takahashi | 128/4 |
| 5,201,908 | 4/1993 | Jones | 128/4 |
| 5,359,991 | 11/1994 | Takahashi et al. | 128/4 |

FOREIGN PATENT DOCUMENTS

| 0 184 778 | 6/1986 | European Pat. Off. . | |
| 0 310 515 | 4/1989 | European Pat. Off. . | |
| 0 338 567 | 10/1989 | European Pat. Off. . | |
| 0 341 718 | 11/1989 | European Pat. Off. . | |
| 0 341 719 | 11/1989 | European Pat. Off. . | |
| 349479 | 1/1990 | European Pat. Off. . | |
| 0 440 252 | 8/1991 | European Pat. Off. . | |
| 0 440 254 | 8/1991 | European Pat. Off. . | |
| 0 444 429 | 9/1991 | European Pat. Off. . | |
| 3722904 | 7/1988 | Germany | 600/153 |
| 51-47587 | 4/1976 | Japan . | |
| 51-103891 | 8/1976 | Japan . | |
| 52-95284 | 7/1977 | Japan . | |
| 58-440033 | 3/1983 | Japan . | |
| 58-44033 | 3/1983 | Japan . | |
| 62-177701 | 11/1987 | Japan . | |
| 1-140902 | 9/1989 | Japan . | |
| 2-57228 | 2/1990 | Japan . | |
| 2-54734 | 11/1990 | Japan . | |
| 3-13105 | 2/1991 | Japan . | |
| 3-29634 | 2/1991 | Japan . | |
| 3-29635 | 2/1991 | Japan . | |
| 3-37029 | 2/1991 | Japan . | |
| 3-37030 | 2/1991 | Japan . | |
| 3-221024 | 9/1991 | Japan . | |
| 3-101901 | 10/1991 | Japan . | |
| 3-101902 | 10/1991 | Japan . | |
| 3-101903 | 10/1991 | Japan . | |
| 3-101904 | 10/1991 | Japan . | |
| 3-101905 | 10/1991 | Japan . | |
| 3-101906 | 10/1991 | Japan . | |
| 3-101907 | 10/1991 | Japan . | |
| H4-325138 | 11/1992 | Japan . | |

*Primary Examiner*—Beverly M. Flanagan
*Attorney, Agent, or Firm*—Armstrong, Westerman, Hattori, McLeland & Naughton

[57] ABSTRACT

A cover-type endoscope apparatus comprises a cover and a covering endoscope used by being inserted into the cover. At least one hand-side tube line of tube lines forming a plurality of channels provided in the cover has a thickness larger than a thickness of an inserting-side tube line.

8 Claims, 19 Drawing Sheets

FIG. 16
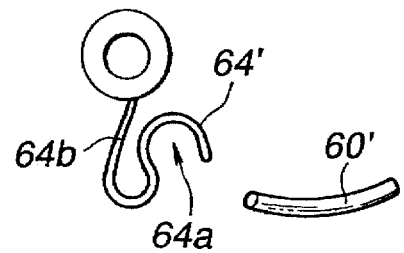
FIG. 17
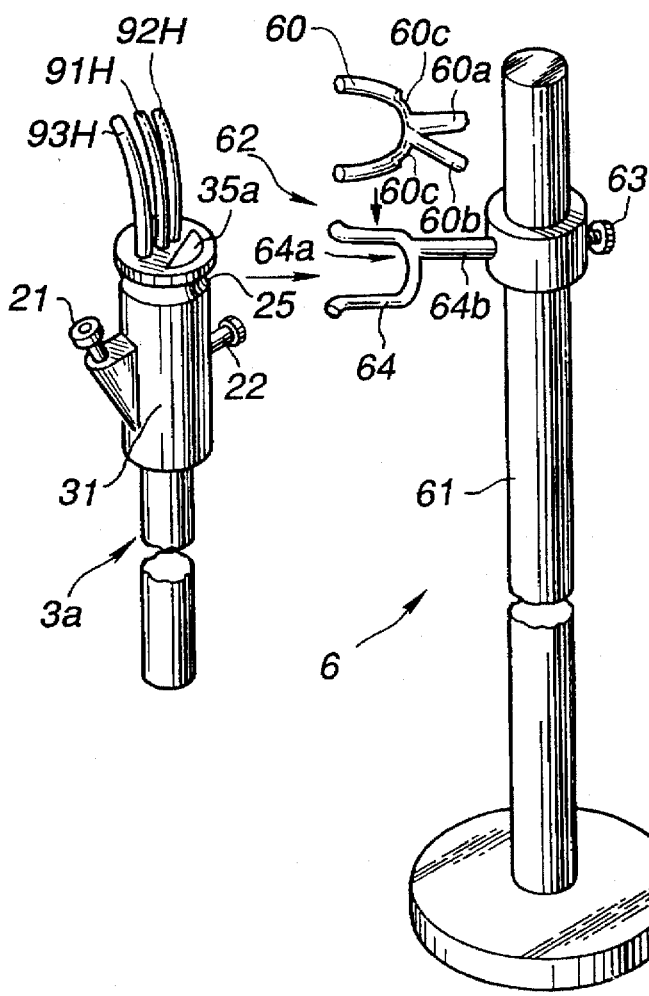
FIG. 18

COVER-TYPE ENDOSCOPE APPARATUS

BACKGROUND OF THE INVENTION

1. Field of the Invention

The present invention relates to a cover-type endoscope apparatus for testing inside a body cavity with a cover-applied endoscope.

2. Description of the Related Art

In recent years endoscopes have been widely used in not only industrial fields but also in medical fields.

An endoscope used in the medical field is inserted into a living body for observation and treatment of diseased parts. The insertion of the endoscope into the living body results in the adherence of; humors and mucus of a patient to an observing window provided at a tip of an inserting portion of the endoscope to impede satisfactory observation of the diseased parts. To cope with such a problem, the endoscope apparatus has gas supply/water supply functions for supplying liquid to the observation window or for supplying gas to the observation window to blow off the liquid remained thereon. These gas supply/water supply functions are performed through gas supply/water supply tube lines by operation of a switch provided at the hand-side of the endoscope.

Also, in some types of endoscopes, there is provided a suction tube line for sucking mucus etc. in the living body and discharging them or a treatment equipment tube line (forceps tube line) for passing a treatment equipment therethrough for medical treatment of the diseased part.

Thus, some types of endoscopes comprise a plurality of tube lines, not only gas supply/water supply tube lines but also suction tube lines and treatment equipment channels.

An endoscope having been used for medical treatment should be immediately washed or sterilized to be used for the next patient. However, such operations for completely washing and sterilizing the endoscope have been troublesome and required significant time, thereby reducing the efficiency of the endoscope.

In view of above, there has recently become adopted a cover-type endoscope apparatus in which an endoscope itself is covered with a cover. This covered endoscope is used for each medical case, and the cover covering the endoscope is disused and thrown away after each treatment, so as to make the washing and sterilization of the endoscope unnecessary.

In the cover-type endoscope, only the tube line to be opened in the body cavity of the patient is provided at the cover side, and the covering endoscope including the observing means and the illuminating means is covered with the cover so as not to directly contact with the inside of the patient's living body.

Examples of such a cover-type endoscope are disclosed in U.S. Pat. No. 4,646,722 and No. 3,162,190.

In the aforementioned cover-type endoscope, there have been operated manually by the user not only to cover the covering endoscope with the cover but also to couple the tubes forming the tube lines provided in the cover to a fluid control unit.

However, since the tube forming the respective tube line is of small diameter, the strength of the tube was insufficient. As a result, there would arise such a disadvantage that the tube may get out of the coupling portion or be broken off or damaged when the cover is taken out of the package, when the covering endoscope is inserted into an endoscope-passing hole formed in the cover, or during the endoscope test operation.

In view of these problems, the thickness of the tube must be increased to enhance the strength of the tube forming the tube line. But as the thickness of the tube increases the tube diameter becomes larger such that the diameter of the inserting portion of the cover-type endoscope to be passed into the body cavity would undesirably become larger.

Further, in the above-mentioned cover-type endoscope apparatus, clean water should be used as water to be supplied to the body cavity, therefore, a sterilized water-supply tank containing the clean water was provided in the fluid control unit.

In this case, however, when the clean water in the water supply tank is exhausted, the tank had to be washed and sterilized again to received the clean water.

Accordingly, unnecessarily long time was required to carry out the troublesome operations of removing the water supply tank from the water supply tube line, washing and sterilizing the water supply tank and thereafter filling the tank with clean water.

In addition, in the aforementioned cover-type endoscope apparatus, when the endoscope cover is attached to the covering endoscope or when the covering endoscope is removed from the endoscope cover, the endoscope cover was secured to and held by a cover holder.

However, after completion of the endoscope test, when the covering endoscope is removed from the endoscope cover used for a patient, there has been a fear of adhering mucus of the used endoscope cover to the cover holding portion of the cover holder securely holding the endoscope cover.

Therefore, it has been necessary to wash and sterilize the cover holder to remove the mucks adhered to its cover holding portion, before the newly sterilized endoscope cover is securely held on the cover holder.

SUMMARY OF THE INVENTION

It is therefore an object of the present invention to provide a cover-type endoscope apparatus having an enhanced tube strength without Increasing the diameter of inserting portion of the cover-type endoscope.

It is another object of the present invention to provide a cover-type endoscope apparatus which is capable of quickly supplying clean water required for the test.

It is further another object of the present invention to provide a cover-type endoscope apparatus which is capable of preventing the cover holder for securely holding the endoscope cover from being contaminated through its cover holding portion.

In summary, the cover-type endoscope apparatus according to the present invention comprises a cover, a covering endoscope used by being inserted into the cover, wherein the thickness of at least one hand-side tube line of tube lines forming a plurality of channels provided on the cover is larger than the thickness of an inserting-portion side tube line.

The above and other advantages, features and additional objects of this invention will be manifest to those versed in the art upon making reference to the following detailed description and accompanying drawings in which a structural embodiment incorporating the principles of this invention is shown by way of illustrative example.

BRIEF DESCRIPTION OF THE DRAWINGS

FIGS. 1 through 8 show a first embodiment of the present invention, wherein:

FIG. 1 is a general perspective view of a cover-type endoscope apparatus;

FIG. 2 is an explanative view showing a schematic composition of a covering endoscope;

FIG. 3 is a perspective view showing a distal end of the covering endoscope;

FIG. 4 is a cross-sectional view showing a schematic composition of an inserting-portion covering portion of the endoscope cover;

FIG. 5 is a perspective view showing a distal end of the inserting portion covering portion into which the covering endoscope is inserted;

FIG. 6 is a cross-sectional view showing an inside of a fixing mouth portion;

FIG. 7 is a cross-sectional view showing a coupled state of inserting-side tube lines with hand-side tube lines;

FIG. 8 is an explanative view showing tubes provided in the cover-type endoscope apparatus;

FIG. 10 and 11 show another example of coupling state of the inserting-side tube lines with the hand-side tube lines, wherein:

FIG. 10 is a cross-sectional view showing a coupling joint for coupling the inserting-side tube lines and the hand-side tube lines;

FIG. 11 is a cross-sectional view cut out at 11A—11A line in FIG. 10;

FIGS. 13 through 16 show a second embodiment of the present invention, wherein:

FIG. 13 is a perspective view showing a state where a clean water pack is provided in the fluid control unit;

FIG. 14 is a cross-sectional view showing the clean water pack and the clean water pack storage;

FIG. 15 is an explanative view showing a schematic composition of gas supply/water supply tube lines of the cover-type endoscope apparatus;

FIG. 16 is an explanative view showing gas supply/water supply control switch and gas supply/water supply states;

FIGS. 17 through 22 show a third embodiment of the present invention, wherein:

FIG. 17 is a perspective view showing a composition of a cover holder;

FIG. 18 is an explanative view of another example of a cover holding member and a holding portion cover;

FIG. 19 is a perspective view showing another composition of the cover holder;

FIG. 20 is a perspective explanative view of the cover holding member;

FIG. 21 is a perspective view for another example of the cover holding member;

FIG. 22 is a cross-sectional view showing an inner configuration of the hunger portion;

FIGS. 24 and 25 show another example of the cover holder, wherein:

FIG. 24 is a perspective view showing a composition of the cover holding member;

FIG. 25 is a perspective view showing a composition of another example of the cover holding member;

FIGS. 26 through 30 show another example of the cover holder, wherein:

FIG. 26 is a perspective view showing the cover holder;

FIG. 27 is a cross-sectional view showing a method for securing the cover holder to the bed;

FIG. 28 is a perspective view showing a relationship between the cover holding member and the holding portion cover;

FIG. 29 is a perspective view showing a general composition of another example of the cover holder;

FIG. 30 is an explanative view showing a stored state of the cover holder;

FIGS. 31 through 33 show a fourth embodiment of the present invention, wherein:

FIG. 31 is a perspective view showing a composition of a cover-attached tray;

FIG. 32 is an explanative view showing a resin sheet attaching state using a attaching tray;

FIG. 33 is an explanative view showing a resin sheet attached state;

FIGS. 34 through 37 show a fifth embodiment of the present invention, wherein:

FIG. 34 is a perspective view showing a state where a bar code seal is attached to the fixing mouth portion of the inserting portion covering portion;

FIG. 35 is a plan view showing a state with the cover being stored in the package;

FIG. 36 is a perspective view showing a state where the bar code seal is attached to the package; and FIG. 37 is an explanative view for an administrative system.

DETAILED DESCRIPTION OF THE PREFERRED EMBODIMENTS

A first embodiment of the present invention will now be described with reference to FIGS. 1–8.

Figure 1:
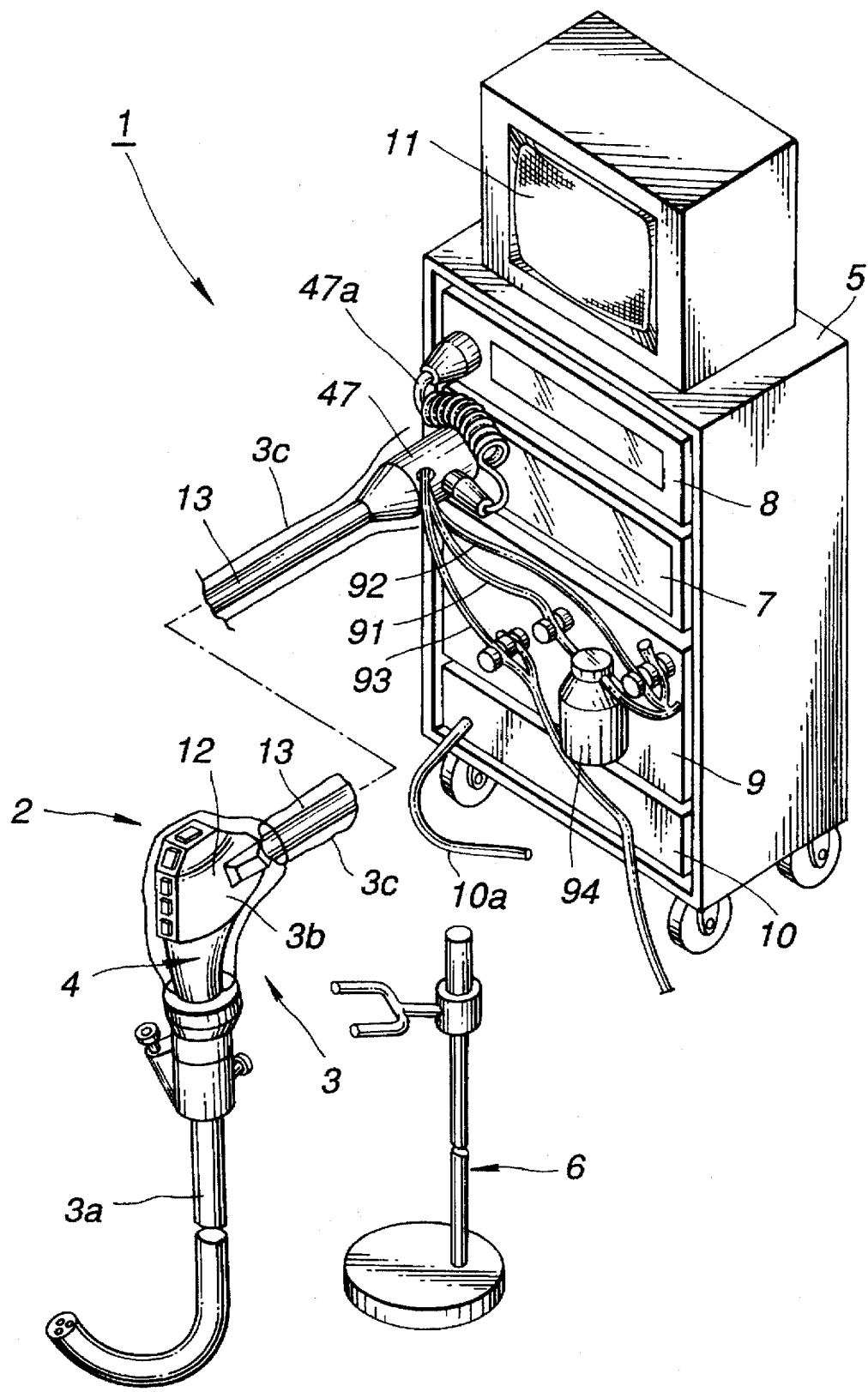

As shown in FIG. 1, a cover-type endoscope apparatus 1 is composed of a cover-type endoscope 2 and a variety of peripheral devices. The cover-type endoscope 2 comprises a cover 3 and a covering endoscope 4 and the like.

Figure 2:
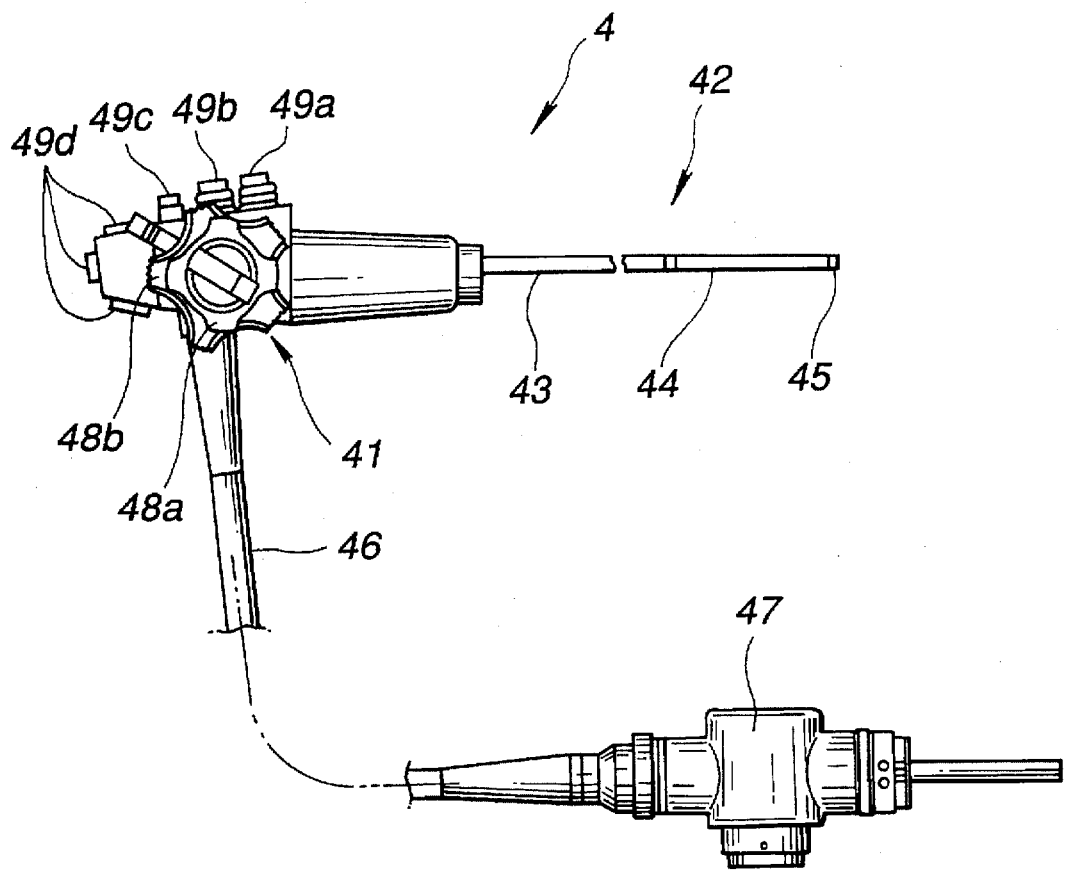
Figure 3:
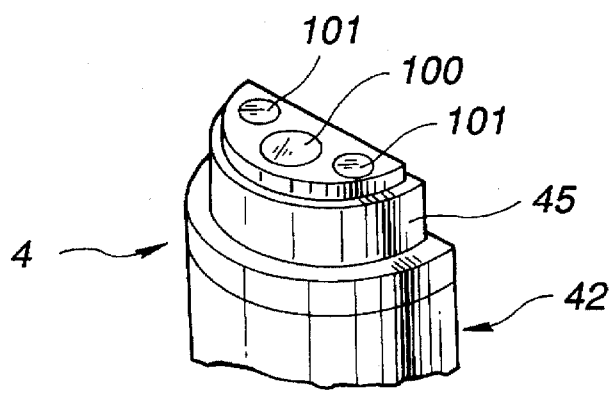

As shown in FIG. 2, the covering endoscope 4 is, for example, an electronic endoscope 4 which has an elongated inserting portion 42 extending in front of an operating portion 41 serving also as a grip portion at the hand-side. The inserting portion 42 is composed of a flexible tube 43, a curved portion capable of being up/down and laterally bent and coupled to the distal end of the flexible tube, and a hard distal portion 45 formed in front of the curved portion 44. As shown in FIG. 3, the inserting portion 42 of the covering endoscope 4 is substantially of semi-cylindrical shape and has an observation optical system 100 and two illumination optical systems 101 provided at the distal surface of the distal portion 45.

Further, a universal cord 46 containing a signal cable and a light guide fiber bundle etc. therein is extended from a side portion of the operating portion 41 and can be coupled to a light source device or a video processor mentioned later through a connector 47 provided at the end portion of the universal cord 46.

In addition, the operating portion 41 has an angle knobs 48a, 48b removably mounted for the bending operation of the bending portion 44, a suction control switch 49a, a water supply control switch 49b, a gas supply control switch 49c and various function switch 49d for photographing.

As shown in FIG. 1, the cover-type endoscope apparatus 1 comprises a cart 5 for storing a variety of peripheral devices to be coupled to the cover-type endoscope 2 and a cover holder 6 for holding the cover-type endoscope 2.

In the cart 5, various peripheral device such as a light source device 7, a video processor 8, a fluid control unit 9 and a channeled endoscope cover expander (hereinafter referred to as expander) 10 etc. are stored.

A monitor 11 for displaying endoscope images is mounted on a roof plate of the cart 5.

The light source device 7 supplies illumination light to the illumination optical system 100 of the covering endoscope 4 to be inserted into the body cavity. By coupling a connector 47 provided in the covering endoscope 4 to the light source device 7, the illumination light is transmitted to the illumination optical system 101 to illuminate the inside of the body cavity.

The video processor 8 displays endoscope images captured by the observation optical system 100 of the covering endoscope 4 having been inserted into the body cavity on the screen of the monitor 11. By coupling a connecting cable 47a to the connector 47 of the covering endoscope 4 and then to the video processor 8, electrical signals of imaging elements are converted into image signals so as to display the endoscope images on the monitor 11.

Further, the fluid control unit 9 acts to perform, for example water supply, gas supply and suction through a water supply tube line 91, gas supply tube line 92 and a suction tube line 98, respectively. The water supply tube line 91 can supply water stored in a water supply tank 94 provided in the middle of the tube line 91 to an exit thereof through a water supply pump coupled to an end portion of the tube line 91. Likewise, gas can be supplied to an exit of the gas supply tube line 92 through a gas supply pump coupled to an end portion of the gas supply duct line 92, and mucks etc. can be sucked through an opening of the suction tube line 98 opened inside the body cavity by means of a suction pump coupled to an end portion of the suction tube line In addition, the expander 10 acts to supply air into the cover 3 through an expanding tube 10a to enable easy attachment or removal of the covering endoscope 4.

On the other hand, the cover 3 covering the covering endoscope 4 of the cover-type endoscope 2 is composed of an inserting portion covering portion 3a for covering the inserting portion 42 of the covering endoscope 4, an operating portion covering portion 3b for covering the operating portion 41 of the covering endoscope 4, a universal cord 46 of the covering endoscope 4 and a universal cord covering portion 3c for covering the tube lines 91, 92 and 93 extended from the covering endoscope 4.

Figure 4:
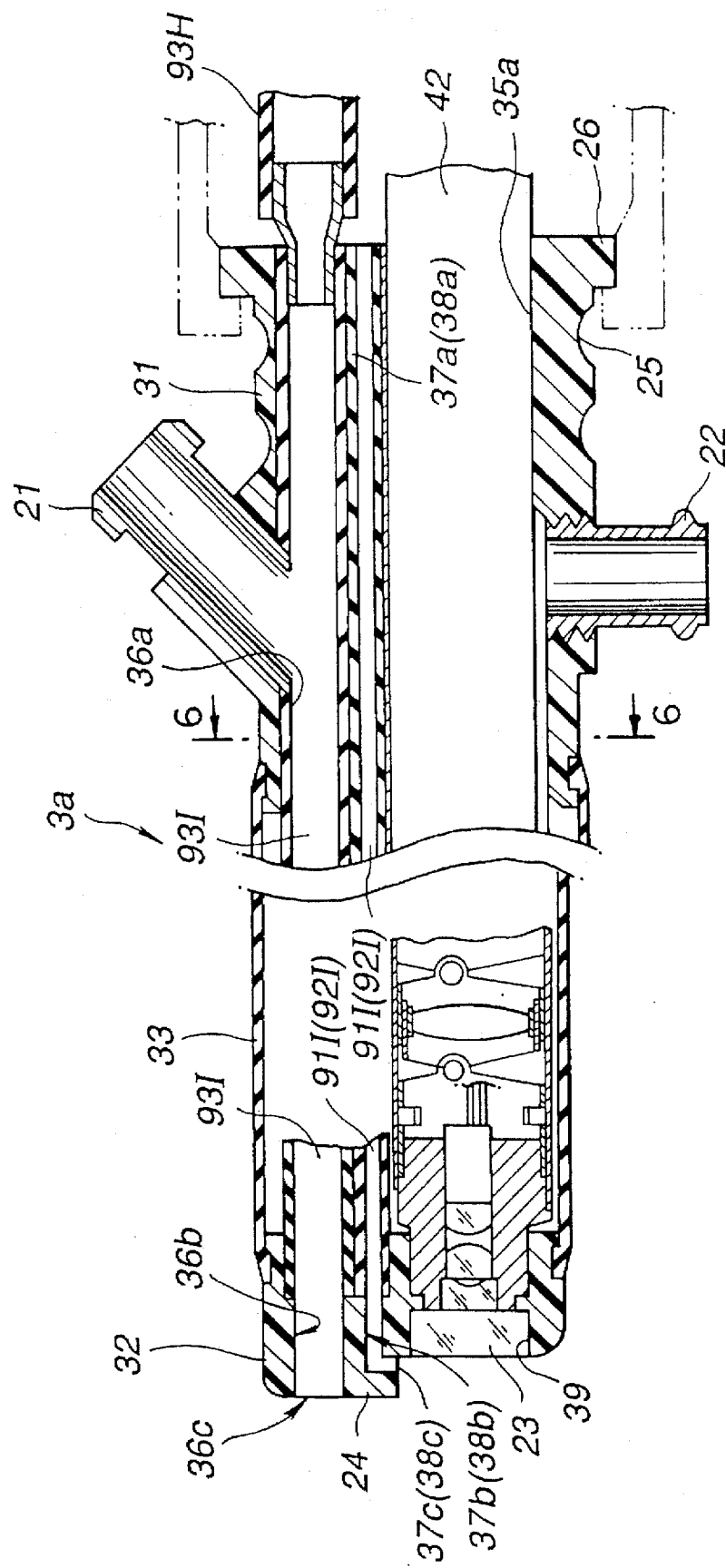
Figure 5:
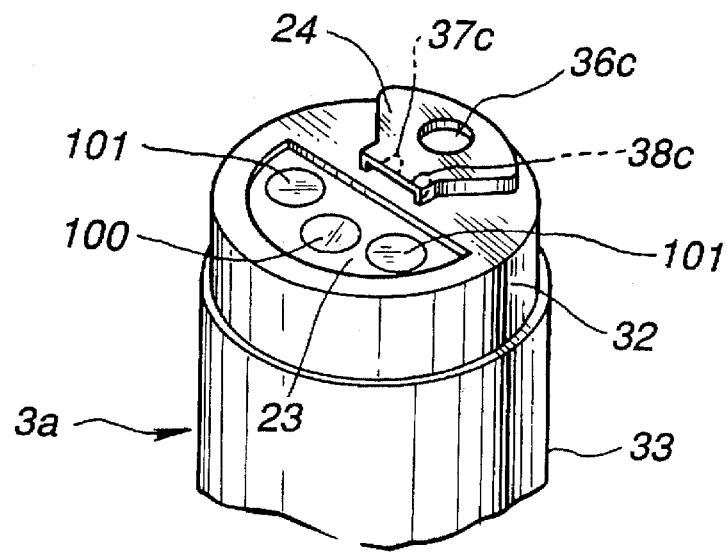

It is now described the inserting portion covering portion 3a of the cover 3 having a predetermined position into which the covering endoscope 4 as shown in FIGS. 4 and 5.

As shown in FIG. 4, the inserting portion covering portion 3a is composed, for example, by coupling an endoscope operating portion fixing mouth portion (hereinafter referred to as fixing mouth portion) 31 formed by resin and provided at the hand-side to a distal end composing portion 32 provided at the distal portion through an elongated flexible cover skin air-tightly.

The fixing mouth portion 31 includes an endoscope passing hole 35a for passing the inserting portion 42 of the covering endoscope 42 there through, a suction hole 36a acting also as a treatment equipment channel, a water supply hole 37a and a water supply hole 38a, all formed therein.

Further, while a treatment equipment inserting opening 21 and a expanded tube mouth body 22 are projected from a side portion of the fixing mouth portion 31, a cover holding member resting portion 25 for holding the fixing mouth portion 31 and an operating portion cover resting portion 26 are formed.

On the other hand, the distal end composing portion 32 opposed to the fixing mouth portion 31 includes an endoscope positioning hole 35b for receiving the distal end portion 42 of the covering endoscope 4, and a suction hole 36b, a water supply hole 37b and a gas supply hole 38b respectively corresponding to the suction hole 36a, the water supply hole 37a and the gas supply hole 38a provided in the fixing mouth portion 31.

Moreover, a lens hole 38 for providing an observation window 23 and a gas supply/water supply nozzle 24 are formed at the distal end side of the distal end composing portion 32. As shown in FIG. 5, the observation optical system 100 and the illumination optical system 101 of the covering endoscope 4 face the observation window 23 provided in the lens hole 39, and the gas supply/water supply nozzle 24 includes an exit portion 37c of the water supply hole 37b, an exit portion 38c of the gas supply hole 38b and the opening portion 36c of the suction hole 36b. A flexible tube is then coupled and secured to the suction hole 36b, the water supply hole 37b and the gas supply hole 38b of the distal end composing portion 32 and is extended to the hand-side end portion of the fixing mouth portion 31 to form inserting-side tube lines, i.e. an inserting side suction tube line 93I, an inserting-side water supply tube line 91I and an inserting side gas supply tube line 92I.

Figure 6:
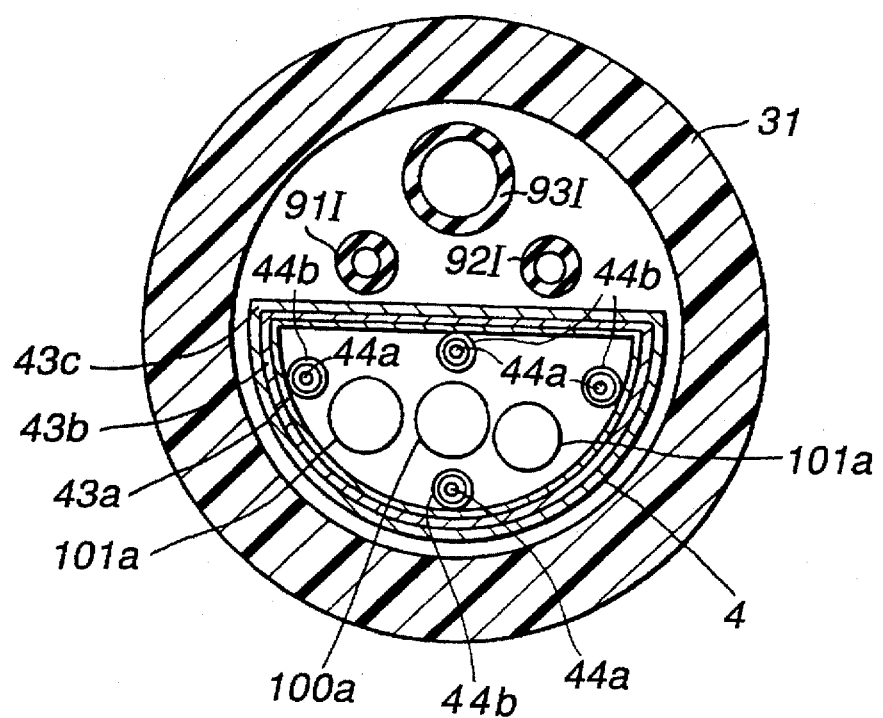

Also, as shown in FIG. 6, the inside of the inserting portion covering portion 3a is separated from the external environment, and the covering endoscope 4, the inserting side suction tube line 93I, the inserting side water supply tube line 91I and the inserting side gas supply tube line 92I are inserted into the inserting portion covering portion.

Furthermore, inside the covering endoscope 4, a signal cable 100a, a light guide fiber 101a for supplying illumination light to the observation optical system 101 and a curved wire 44a for curving the curved portion 44 are provided.

In the shown embodiment, the numerals designate respectively: 44b, an angle wire guide; 43a, 43b and 43c, a helical tube, a woven tube and a skin respectively, all forming the flexible tube 43 of the covering endoscope 4.

Figure 7:
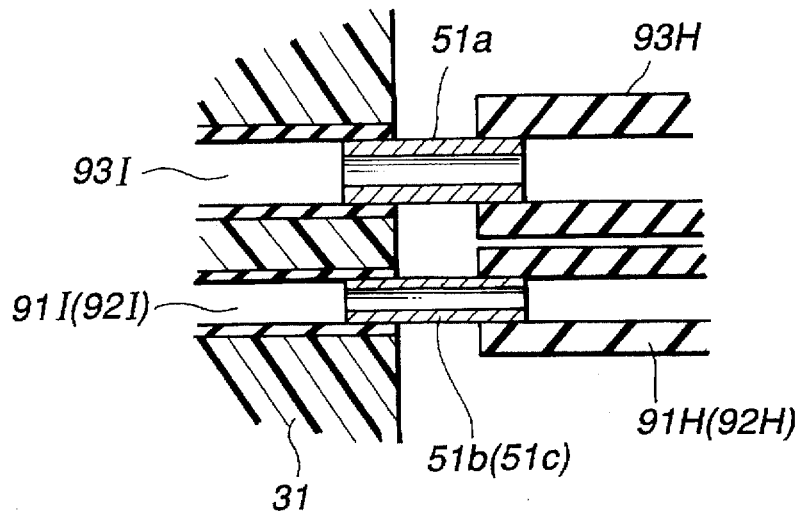

As shown in FIG. 7, there are further arranged coupling joints 51a, 51b and 51c at the hand-side of the fixing mouth portion 31 for the inserting side suction tube line 93I, the inserting side water supply tube line 91I and the inserting side gas supply line tube 92I respectively. From these coupling joint 51a, 51b and 51c, a hand-side water supply tube line 91H, a hand-side gas supply tube line 92H and a hand-side suction tube line 93H are extended toward the fluid control unit.

Namely, the water supply tube 91I is composed of the inserting-side water supply tube line 91I, the coupling joint 51b and the hand-side water supply tube line 91H. In the same manner, the gas supply tube line 92 is composed of the inserting side gas supply tube line 92I, the coupling joint 51c and the hand-side gas supply tube line 92H, and the suction tube line 93 is composed of the inserting-side suction tube line 98I, the coupling joint 51a and the hand-side suction tube line 93H.

The tube lines will now be described with reference to FIG. 8.

Figure 8:
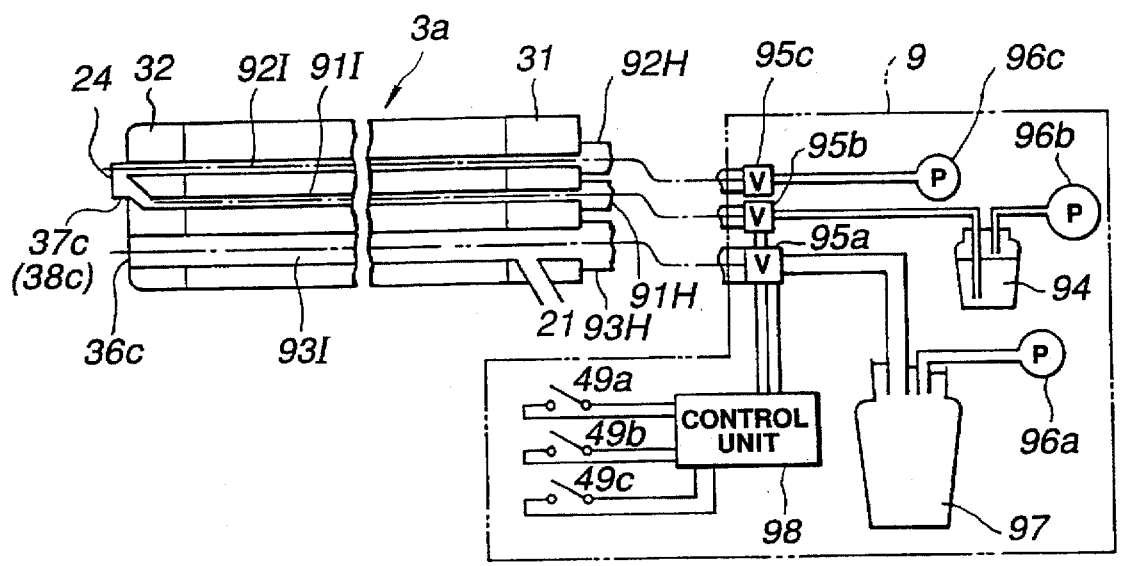

As shown in FIG. 8, the suction tube line 93, the water supply tube line 91 and the gas supply tube line 92 extending toward the fluid control unit 9 from the exit portions 37c and 38c of the gas supply/water supply nozzle 24 and the opening portion 36c formed at the distal end composing portion 32 of the inserting portion covering portion 3a are composed of the inserting-side suction tube line 93I, the inserting-side gas supply tube line 92I and the inserting-side water supply tube line 91I passing through inside the inserting portion covering portion 3a, and of the hand-side suction tube line 93H, hand-side gas supply tube line 92H and the hand-side water supply tube line 91H.

Further, the hand side gas supply tube line 92H is coupled to a gas supply pump 96c through a pinch valve 95c, the hand-side water supply tube line 91H is coupled to a water supply tank 94 storing sterilized water and a water supply pump 96b through a pinch valve 95b, and the hand-side suction tube line 93H is coupled to a suction pump 96a through a suction bottle 97 communicated with a pinch valve 95a.

The pinch valves 95a, 95b and 95c are electrically connected to the control unit 98. Therefore, by turning the suction control switch 49a, the water supply control switch 49b or the gas supply control switch 49c provided in the operating portion 41 of the covering endoscope 4 on and off, the pinch valves 95a, 95b and 95c respectively corresponding to the switches 49a, 49b and 49c will operate to open and close.

As shown in FIG. 7, among the tube lines formed by coupling the inserting-side water supply tube line 91I, the inserting-side gas supply tube line 92I and the inserting side suction tube line 93I to the hand-side water supply tube line 91H and the hand-side gas supply tube line 92H and the hand-side suction tube line 93H respectively, at least one tube line has a larger wall thickness at the hand-side tube line than the wall thickness at the inserting-side tube line to be coupled to the coupling joints 51b, 51c and 51a.

In this embodiment, for all the water supply tube line, the gas supply tube line and the suction tube line, the wall thickness is larger at the hand-side tube line than at the inserting-side tube line.

The operation of the cover-type endoscope apparatus composed as mentioned above will now be described.

For example, when mucus has been adhered to the observation window 23 provided at the distal end surface of the inserting portion covering portion 3a, the observer should firstly supply water onto the observation window 23 to eliminate the mucus thereon. Therefore, the observer turns the water supply control switch 49 provided in the operating portion of the covering endoscope 4 on. In response to this operation, the pinch valve 95b opens and the sterilized water in the water supply tank 94 being pressured by the water supply pump 96b will be discharged from the exit portion 37c formed at the gas supply/water supply nozzle 24 provided in the distal end composing portion 32 through the hand-side water supply tube line 91H, the coupling joint 51b and the inserting portion water supply tube line 91I, for eliminating the mucus on the observing window 23. For stopping the water supply, the water supply control switch 49b is turned off to close the pinch valve 95b so as to stop the water supply.

Subsequently, gas is supplied to the observation window 23 for eliminating the water remained thereon. At this time, the observer turns the gas supply control switch 49c on provided in the operating portion 41 of the covering endoscope 4. Then the pinch valve 95c opens and the air from the gas supply pump 96c passes through the hand-side gas supply tube line 92H, the coupling joint 51c and the inserting-side gas supply tube line 92I and discharged from the exit portion 38c formed at the gas supply/water supply nozzle 24 to blow out the water drops on the observation window 23. For stopping the gas supply, the gas supply control switch 49c is turned off to close the pinch valve 95c.

Further, it is necessary to suck the water having been supplied to the observation window 23 and the mucus etc. in the living body. The observer then turns on the suction switch 49a on provided at the operating portion 41 of the covering endoscope 4. In response to this, the pinch valve 95a opens and the suction operation is started by the suction pump 96a so as to flow the water and the mucus etc. in the living body into the suction bottle 94 through the opening portion 36c, the inserting-side suction tube line 93I, the coupling joint 51a and the hand-side suction tube line 93H. For stopping the suction, the suction switch 49a is turned off to close the pinch valve 95a.

In this manner, by separating the tube lines communicating the body cavity and the fluid control unit into the inserting-side tube lines using thin wall tubes and the hand-side tube lines using thick wall tubes, and communicating and coupling both by a coupling joint, it is possible to compose only the tubes of the hand-side tube lines of significantly reinforced large diameter tubes without increasing the tube diameter of the inserting-side tube line, the hand-side tube lines having large diameters could be prevented from being damaged or broken due to its increased strength.

In addition, even if large force is imposed on the hand-side tube line disposed outside the body cavity when the cover-type endoscope is twisted or pulled during the endoscope inspection, the hand-side tube line would not be fallen out from the coupling joint or the pinch valve due to the large force applied on the coupling portion by virtue of the tubes having large wall thickness and strength.

Another example of the coupling joint will now be described with reference to FIG. 9.

Figure 9:
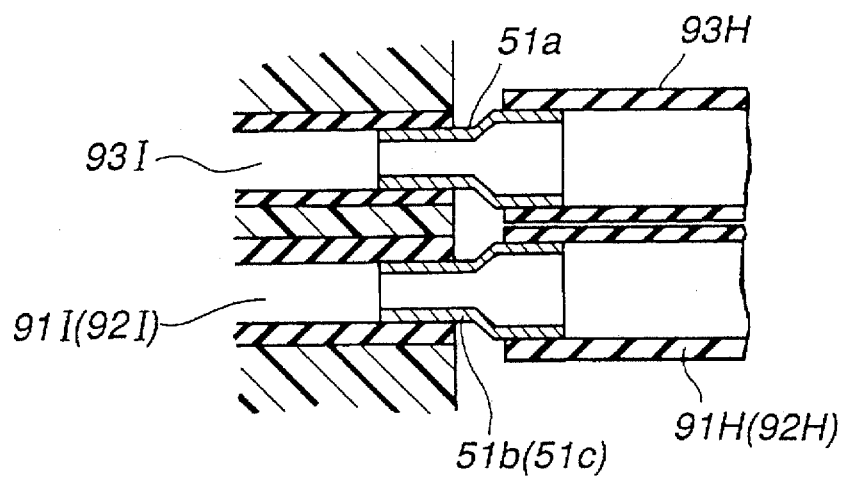
FIG. 9 is a cross-sectional view showing another coupled state of the inserting-side tube lines and the hand-side tube lines.

As shown in FIG. 9, the inserting-side water supply tube line 91I, the inserting-side gas supply tube line 92I and the inserting-side suction tube line 93I are communicated and coupled to the hand-side water supply tube line 91H, the hand-side gas supply tube line 92H and the hand-side suction tube line 93H through the coupling joints 51b, 51c and 51a respectively which has larger diameters at the hand-side and smaller diameters at the inserting side.

In this manner, by forming the tube forming the hand-side tube line to have a diameter larger than that of the tube forming the inserting-side, it is possible to increase the amounts of the water supply, the gas supply and the suction at the water supply outlet 37c, gas supply outlet 38c and the opening 36c formed at the distal end composing portion 32 so as to enhance the operation efficiency and speed up the inspection.

If it is sufficient with the conventional amounts of the gas supply, the water supply and the suction, composing the tube forming the hand-side tube line of that having large diameter and thickness would enable the tube forming the inserting-side tube line to be replaced with that of less diameter, so as to make it possible to reduce the diameter of the inserting portion covering portion 3a of the cover-type endoscope 2.

A desired tube line can be formed by properly selecting the material, the thickness, the inner diameter and the outer diameter of the tube forming the tube line.

Also it is possible to use tubes having varied inner and outer diameters etc. in the middle thereof for the hand-side tube lines.

Another example of the coupling joint will now be described with reference to FIGS. 10 and 11.

Figure 10:
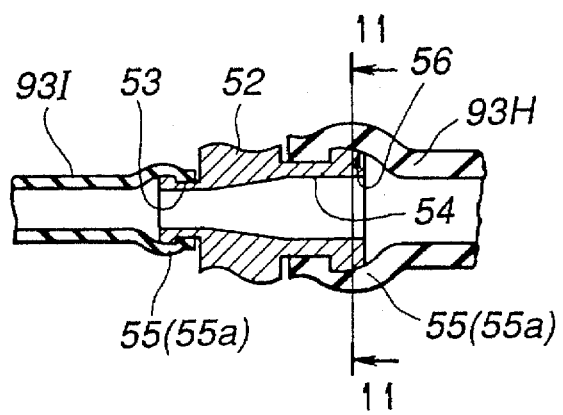

As shown in FIG. 10, for example, the coupling joint 52 according to this embodiment Includes tube stopping means 55 at the coupling portion distal portion 53 coupling to the inserting-side suction tube line 98I and at the coupling portion hand-side portion 54 coupling to the hand-side suction tube line 93H. The tube stopping means 55 is composed of a flange portion 55a formed at the circumference of the coupling portion distal end portion 53 and the coupling portion hand-side portion 54.

Figure 11:
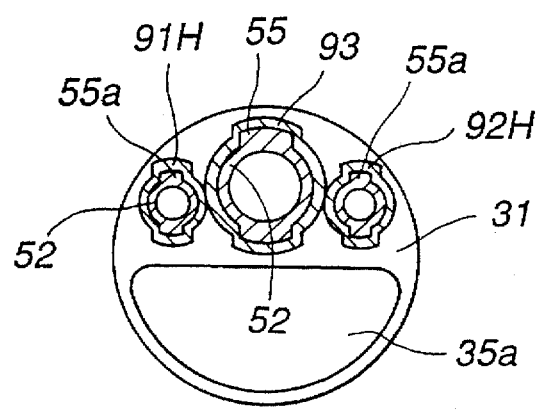

As shown in FIG. 11, the flange portion 55a is formed over not all the outer periphery of the coupling portion distal portion 53 and the coupling portion hand-side portion 54, but at the portion of the tube lines being contiguous by partially cutting out the flange projected therefrom.

When the tube is coupled to the coupling joint 52 formed as mentioned above, the flexible tube becomes convexed only in the direction of the projected portion of the flange portion by the flange portion 55a provided in the coupling joint 52 as shown in FIGS. 10 and 11, so as to achieve the communication and the coupling of both.

In this manner, it is possible to securely coupling and fixing the tubes of smaller diameter at the inserting-side tube line and the tubes of larger diameter at the hand-side tube line by the tube stopping means provided in the coupling joint.

Further, due to the affect of the flange portion acting as the tube stopping means, the tube communicated and coupled to the coupling joint expands only in the direction of flange formation, it is possible to form a small-sized coupling joint without occupying large tube line space unless the flange portion being the tube stopping means is not formed at the tube line-contiguous position.

The attaching property of the tube can be enhanced by forming an introductory portion 56 of C or R-letter surface form at the tube inserting-side mouth portion including the flange portion being the tube stopping means.

Another example of the tube line will now be described with reference to FIG. 12.

Figure 12:
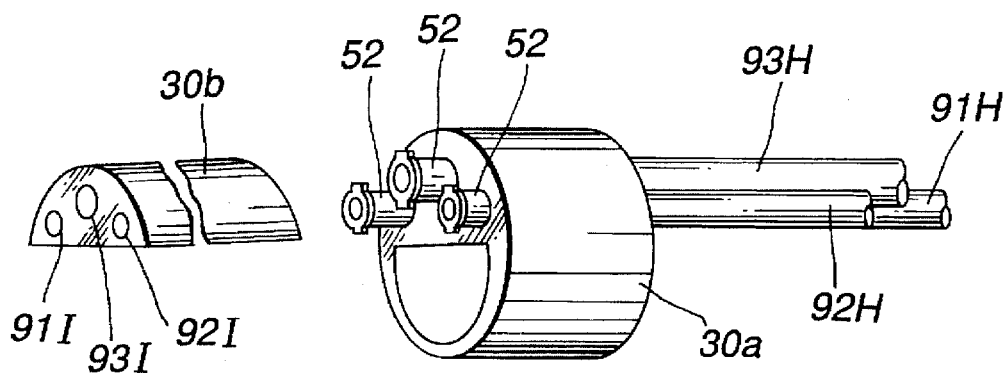
FIG. 12 is a perspective view showing a multi-lumen tube forming the inserting-side tube lines of the inserting portion covering portion.

As shown in FIG. 12, the inserting-side suction tube line 93I, the inserting-side water supply tube line 91I and the inserting side gas supply tube line 92I, together composing the inserting-side tube lines, are integrated to form tubes 30b of multi-lumen inserting-side tube lines. In addition, tubes 30a of fixing mouth portion-side multi-lumen tube lines including a hand-side suction tube line 93H, hand-side water supply tube line 91H and the hand-side gas supply tube line 92H provided with a coupling joint 52 having a tube stopping means 55 to be coupled to the tubes 30b for the multi-lumen inserting-side tube lines is provided. The tubes of the multi-lumen inserting side tube lines 30b are communicated and coupled to the coupling joint 52 of the tubes 30a for the fixing mouth portion-side multi-lumen tubes.

In this manner, it is possible to collectively perform the troublesome tube line coupling operation so as to significantly improve the operating efficiency.

A second embodiment of the present invention will now be described with reference to FIGS. 13-16.

Figure 13:
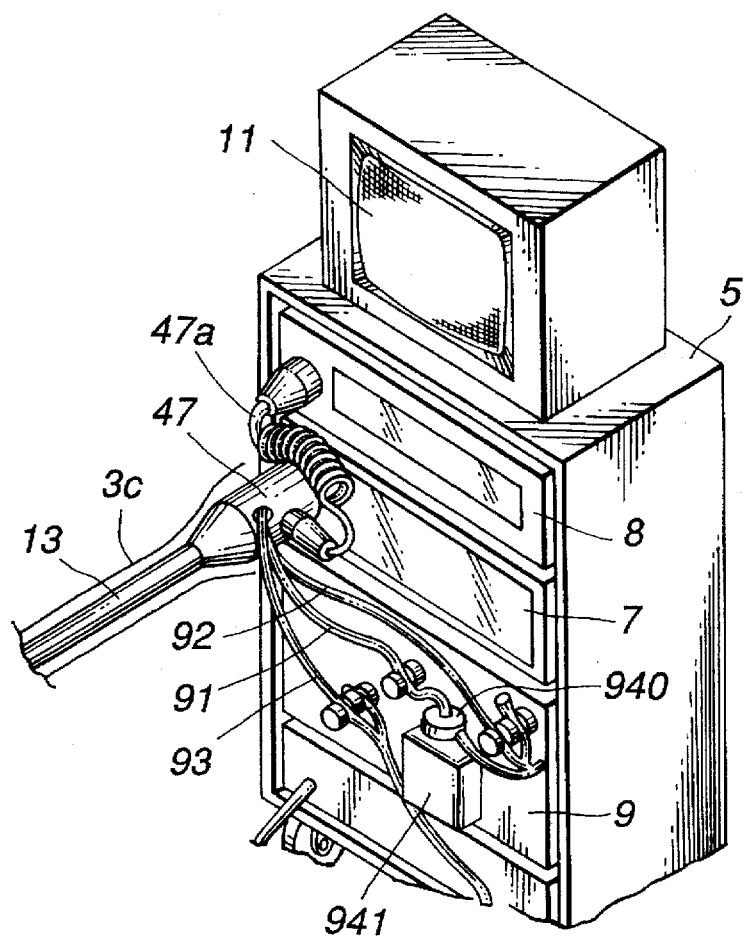

As shown in FIG. 13, the water supply tube line 91 of the fluid control unit 9 can supply clean water or sterilized water contained in the clean water pack 940 in the clean water storage 941 provided in the middle of the tube line to the outlet portion of the water supply duct line 91 through a water supply pump coupled to the end portion of the water supply tube line 91.

Figure 14:
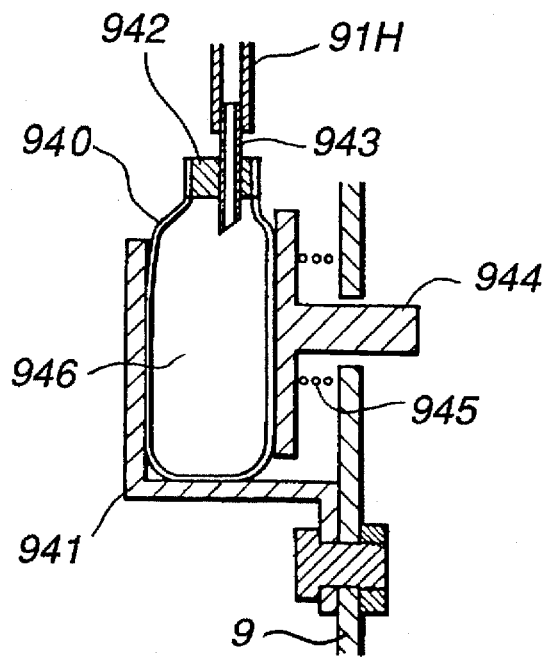

As shown in FIG. 14, the clean water pack 940 contains the clean water or the sterilized water, and is to be stored in the clean water pack storage 941 fixed to the fluid control unit 9 through bolt and nut.

The liquid tank 946 of the clean water pack 940 in the clean water pack storage 941 and the hand-side water supply tube line 91H are separated from each other by a lid portion 942, into which a coupling tube (needle-like) as a coupling means provided at the hand-side portion of the hand-side water supply tube line 91H is inserted and coupled.

Further, the clean water pack storage 941 fixed to the fluid control unit 9 includes a pressure member 944 and a coil spring 945 as a pressure means for supplying the clean water contained in the clean water pack 940 in the clean water pack storage 941. The clean water pack 940 is always pressurized by the press member 944 provided with the coil spring 940.

The gas supply tube line system and the water supply tube line system of the fluid control unit 9 will now be described with reference to FIG. 15.

Firstly, the gas supply tube line system will be mentioned.

Figure 15:
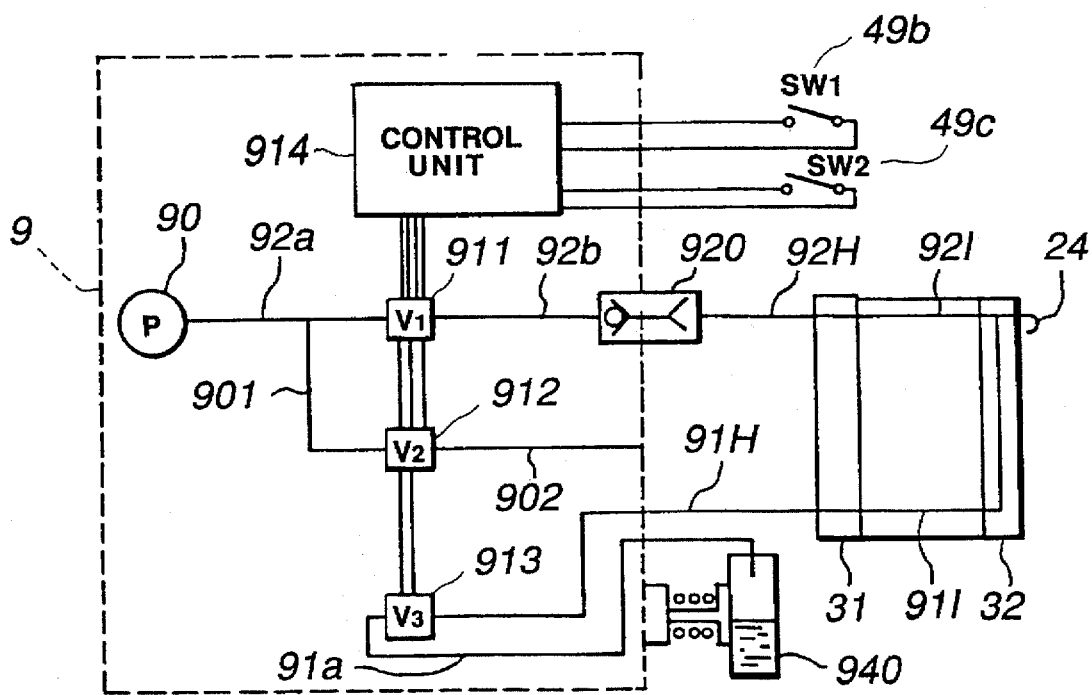

As shown in FIG. 15, a pump 90 is provided inside the fluid control unit 9, and an inner first gas supply tube line (hereinafter referred to as first gas supply tube line) 92 is provided from the pump 90 to the first valve 911. Further, an inner second gas supply tube line (hereinafter referred to as second gas supply tube line) 92 is provided to communicate and couple the first valve 911 to a quick disconnect joint 920. The hand-side gas supply tube line 92H and the inserting-side gas supply duct line 92I are extended from the quick disconnect joint 920 and communicated to the gas supply/water supply nozzle 24. A branch tube line 901 is provided in the middle of the first gas supply tube line 92a and coupled to a release tube line 902 having an open end.

Next, the water supply tube line system will now be described.

As shown in FIG. 15, a clean water pack 940 is provided outside the fluid control unit 9. An inner water supply duct line 91a is arranged from the clean water pack 940 to a third valve 913. In addition, A hand-side water supply tube line 91H and an inserting-side water supply tube line 911 are extended from the third valve 913 to be communicated to the gas supply/water supply nozzle 24.

The first valve 911, the second valve 912 and the third valve 913 are electrically connected to the control unit 914 and to the gas supply control switch 49c and the water supply control switch 49b respectively provided in the operating portion 41 of the covering endoscope 4 in the control unit 914.

As shown in FIG. 16, the first valve 911 or the second valve 912 opens/closes by turning the gas supply control switch 49c on/off. Namely, when the gas supply control switch 49b is turned on, the first valve 911 opens while the second valve 912 closes such that air flows to the gas supply/water supply nozzle 24 through the hand-side gas supply tube line 91H. Further, when the gas supply control switch 49c is turned off, the first valve 911 closes while the second valve 912 opens such that air leaks through the release tube line 902. Further, by turning the water supply control switch 49b on and off, the third valve 913 opens and closes for the water supply operation. In this embodiment, the open/close control means is composed of pinch valves 911, 912 and 913.

The water supply operation of the fluid control unit 9 composed as mentioned above will be now described.

The clean water pack 940 in the clean water pack storage 941 is always pressurized by the pressure member 944 and the coil spring 945 provided in the clean water pack storage 941. Therefore, when the observer turns the water supply control switch of the cover-type endoscope 2 on the third valve opens, such that the clean water and the sterilized water contained in the clean water pack 940 is supplied from the gas supply/water supply nozzle 24 through the hand-side water supply tube line 91H and the inserting-side water supply tube line 91I.

Further, when the clean water or the sterilized water in the clean water pack is exhausted during the endoscope inspection, the used clean water pack 940 is thrown away into a refuse bin and a new clean water pack 940 is stored in the clean water pack storage 941 to be communicated to the coupling tube 943.

In this manner, by use of clean water pack containing the clean water or the sterilized water as a water supply means of the cover-type endoscope apparatus, it is possible to make it unnecessary to fill the water supply tank with the clean water and the sterilized water before starting the inspection.

In addition, by eliminating the troublesome operation of washing and decontaminate the water supply tank and exchanging the clean water or the sterilized water during the inspection interval, the exchange operation time can be shortened, which contributes to lighten the inspector from his burden.

A third embodiment of the present invention will now be described with reference to FIGS. 17–22.

As shown in FIG. 17, the cover holder 6 is composed of a stand portion 61, a cover holding portion 62 being movable with respect to the stand portion 61 for holding the inserting portion covering portion 3a when the covering endoscope 4 1s removed, and a holding portion cover 60 removably mounted on the cover holding portion 62.

The cover holding portion 62 can be freely changed its vertical position and orientation by loosening the screw 63 being a fixing means for fixing the holding portion 62, and can be fixed at a desired position and orientation by tightening the screw 63. Further, the cover holding portion 62 comprises a cover holding member 64 for resting the inserting portion covering portion 3a thereon by engaging it with the cover holding portion resting portion 25 of the fixing mouth portion 31 of the inserting portion cover portion Moreover, if the holding portion cover 60 is composed of a soft and restitutive synthetic resin such as polyester or tetrafluoroethyrene for covering a holding portion 64a and a base end portion 64b of the cover holding member 64 provided in the cover holding portion 62. Therefore, the holding portion 64a and the base end portion 64b of the holding portion cover 60 are formed substantially in the same shape as the cover holding member 64.

Further, in virtue of the holding portion cover 60 being made of soft and restitutive resin material, the base end portion 64b of the cover holding member 64 is, in the normal state, covered with the upper surface cover portion 60a and the lower surface cover portion 60b.

The operation of the cover holder 6 composed as mentioned above will now be described.

Firstly, the operation of inserting the covering endoscope 4 into the endoscope passing hole 35a formed in the inserting portion covering portion 3a of the cover 3 will be explained.

At first, the cover holder 6 and the sterilized holding portion cover 60 are prepared.

Next, the cover holding member 64 of the cover holder 6 is covered with the sterilized holding portion cover 60. At this time, the introductory portion 60c formed in the holding portion cover 60 is positioned at the distal end side of the cover holding member 64 to securely cover the holding portion 64a of the cover holding member 64, and thereafter the base end portion 64b of the cover holding member 64 is covered with the upper surface cover portion 60a and the lower surface cover portion 60b.

After performing the adjustment of the vertical position and the orientation of the cover holding portion 62, the cover holding member resting portion 25 formed in the fixing mouth portion 31 of the inserting portion covering portion 3a is rested on the cover holding member to which the holding portion cover 60 is attached, and the covering endoscope 4 is inserted into the endoscope passing hole 35a, thereby completing the attaching operation.

Subsequently, the operation of removing the covering endoscope 4 having been inserted through the endoscope passing hole 35a of the inserting portion covering portion 3 after completion of the inspection will now be described.

Firstly, the used inserting portion covering portion 3a having a contaminated outer surface is rested on the cover holding member 64 to which the sterilized holding portion cover 60 used on attaching operation is applied.

Next, the covering endoscope 4 is removed from the endoscope passing hole 35a of the inserting portion covering portion 3a rested on the cover holding member 64. Then the inserting portion covering portion 3a having been rested on the cover holding member 64 is removed to be thrown away into a refuse bin.

Further, the holding portion cover 60 covering the cover holding member 64 of the cover holder 6 is removed and thrown away into the refuse bin.

In this manner, since the cover holding member of the cover holder is covered with the sterilized holding portion cover to be inserted/removed into/from the inserting portion covering portion of the covering endoscope, even if the mucks on the cover-type endoscope is adhered to the cover holding member, the cover holder can be always maintained in clean state by removing and thrown away the holding portion cover covering the holding portion and the base end portion of the cover holding member.

In addition, as mentioned above, since the holding portion cover is exchanged at every inspection, any contamination of the cover-type endoscope through the cover holder can be eliminated.

Since the portion to be in contact with the inserting portion covering portion is restricted only to the cover holding member, it is also possible to cover only this holding portion with the holding portion cover.

Another example of the cover holding member will now be described with reference to FIG. 18.

As shown in FIG. 18, the holding portion 64'a and the base end portion 64'b of the cover holding member 64' are formed in smooth line by processing stick-type member.

Due to the holding portion 64'a and the base end portion 64'b of the cover holding member 64a being formed in smooth lines from stick-type members, it is possible to form the holding portion cover 60' in cylindrical shape so as to be easy attached to and removed from the cover holding member 64a.

Another example of the cover holding member will now be described with reference to FIGS. 19–22.

Figure 19:
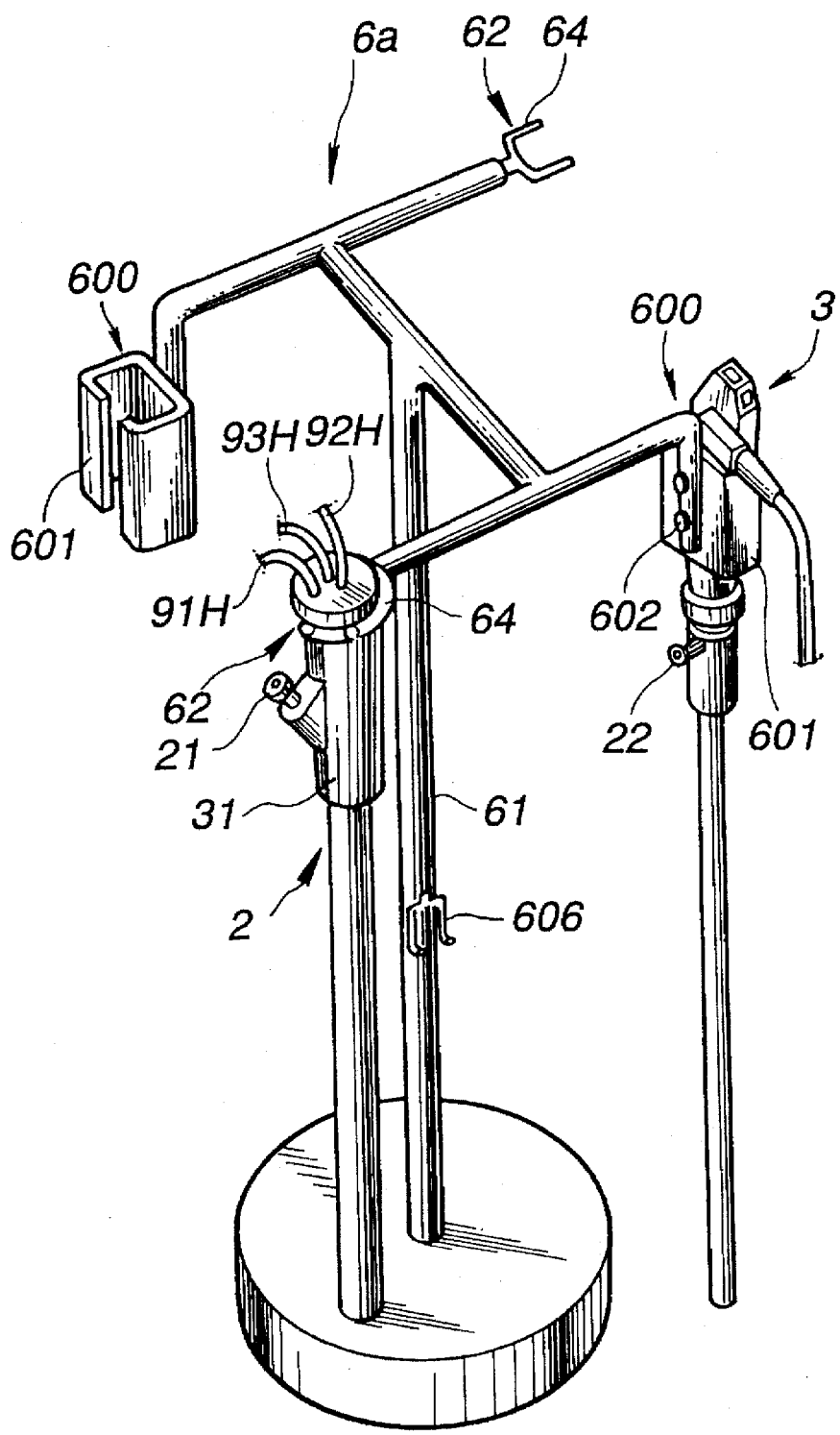

As shown in FIG. 19, the cover holder 6a includes a plurality of hanger portions 600 and a plurality of cover holding portions 64 in the stand 61 for enabling the inspection to be performed even with a plurality of cover-type endoscope 2.

Figure 20:
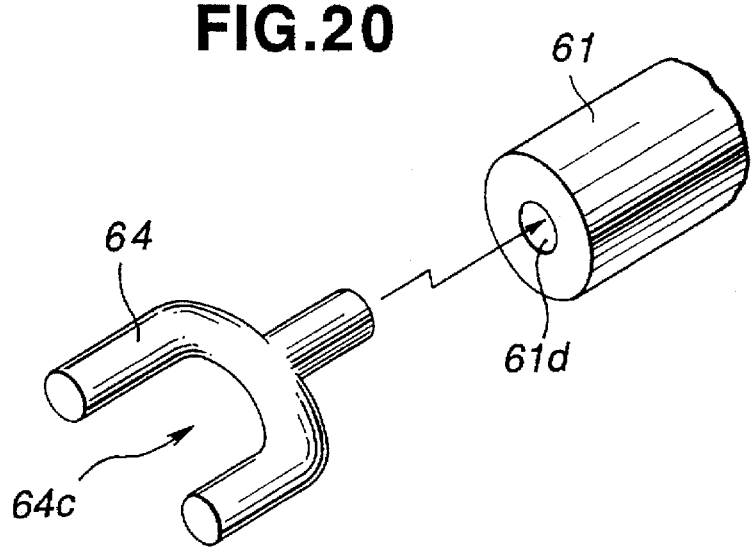
Figure 21:
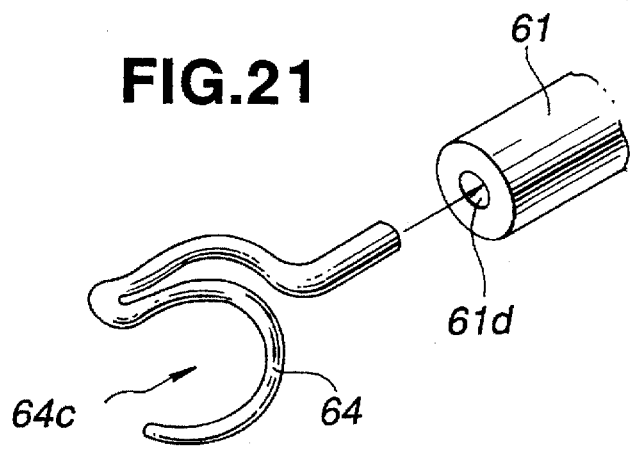

As shown in FIGS. 20 and 21, the cover holding member 64 has an operating portion cover resting portion 64c composed of substantially Y-letter shape member or stick-type member formed in continuously curved line portion. The cover holding portion 62 is formed by inserting the base end portion 64b of the cover holding member 64 into the inserting hole 61d provided in the stand 61. Namely, the cover holding member 64 is removably attached to the stand.

Figure 22:
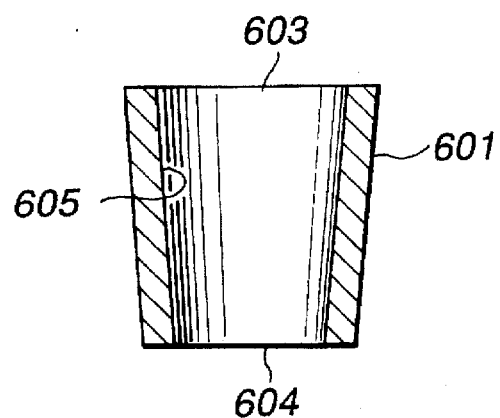

On the other hand, in the hanger portion 600, an endoscope fixing member 601 is mounted through axis 602 and the like. As shown in FIG. 22, the endoscope fixing member 601 has a tapered surface 605 tapering from the inserting-side 608 at the upper surface to the lower surface 604 to less width. Therefore, it is possible to securely fix the cover-type endoscope 2 or the covering endoscope 4 to the tapered surface 605 by mutual contact.

Of course, the conventional endoscopes without cover can be securely fixed.

In the stand 61, the expanding tube fixing member 606 for fixing the expanding tube 10a is formed to be inserted and fixed removably to a hole not shown in the same manner as in the cover holding member 64.

Thus, by making it possible to removably mount the sterilized cover holding member on the stand, it is possible to prevent the contamination through the cover holder by exchanging the cover holder material even when the cover-type endoscope and the cover holding member are contaminated.

In addition, since a plurality of the hanger portions and the cover holding portions are provided in the cover holder, a plurality of cover-type endoscope can be prepared collectively in one time. Accordingly the inspection efficiency can be enhanced by appropriately changing the cover-type endoscope to other of different specifications during the inspection.

Figure 23:
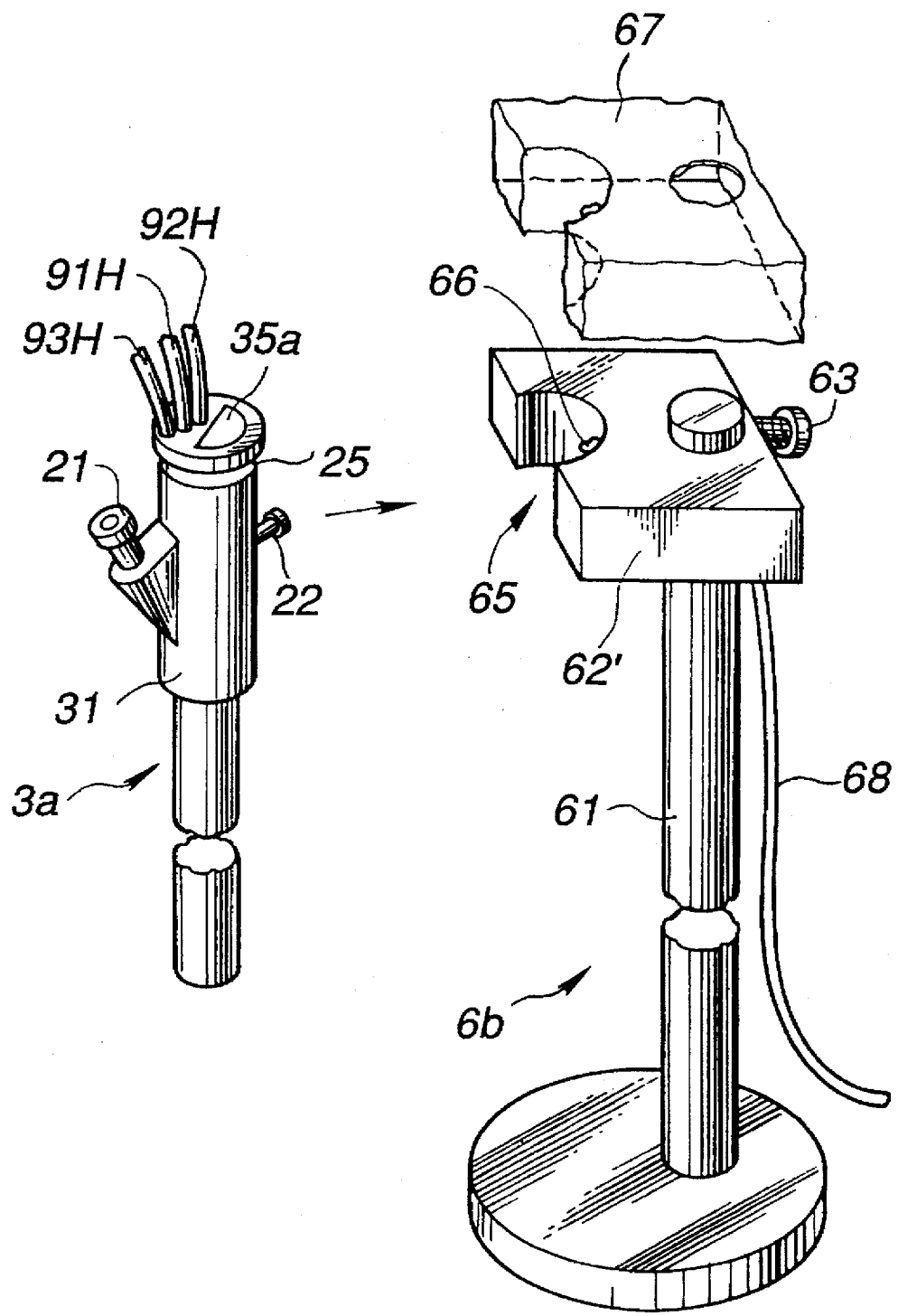
FIG. 23 is a perspective view showing other compositions of the cover holder.

Another example of the cover holder will now be described with reference to FIG. 23.

The operations of the covering endoscope 4 to be inserted into or removed from the endoscope passing hole 35a of the inserting portion covering portion 3a rested on the cover holder 6 have been carried out by supplying air supply from the expander 10 or stopping the air supply with the on/off operation of a switch provided in the expander. As a result, it has been necessary for a clean operator to pay attention not to carelessly contact the switch provided in the expander.

In view of this problem, in the cover holder 6b according to this embodiment, a cover fixing portion 65 is formed in the vertically movable cover holding portion 62', and a switch 66 of an expander is provided in the cover fixing portion 65. The cover holding portion 62' and the switch 66 are covered with a holding cover 67 formed in small thickness by silicon resin etc. The other compositions are the same as in the aforementioned third embodiment.

The operation of the aforementioned cover holder 6b will now be described.

Attaching the inserting portion covering portion 3a of the cover 3 to a predetermined position of the cover fixing portion 65 being covered with the sterilized holding portion cover 67 acts to turn the switch 66 on to supply air from the expander through the expanding tube to the endoscope passing hole 35a of the inserting portion covering portion 3a for expansion. In the same manner, when the covering endoscope 4 is removed from the cover-type endoscope 2 used for a patient, attaching the inserting portion covering portion 3a to the cover fixing portion 65 turns the switch 65 on to supply air from the expander through the expanding tube to the endoscope passing hole 35a of the inserting portion covering portion 3a for expansion.

In this manner, since the switch of the expander is turned on and off by the attaching operation of the inserting portion covering portion to the cover holding portion of the cover holder, the attaching/removing operation of the covering endoscope can be simplified. Further, the clean operator can concentrate on the inspection and medical treatment due to no fear of carelessly touching the contaminated switch of the expander. The other operations and advantages are the same as in the previous embodiment.

The switch 66 is normally in off-state and turns on by being pushed to turn the expander on through the connecting cord 68 for supplying air to the expanding tube.

Another example of the cover holder will now be described with reference to FIG. 24.

It is troublesome to prevent the inserting portion covering portion 3a from being contaminated by contacting with floor upon attachment of the sterilized inserting portion covering portion 3a having a long inserting length to the cover holder 6 for the insertion of the covering endoscope 4.

Figure 24:
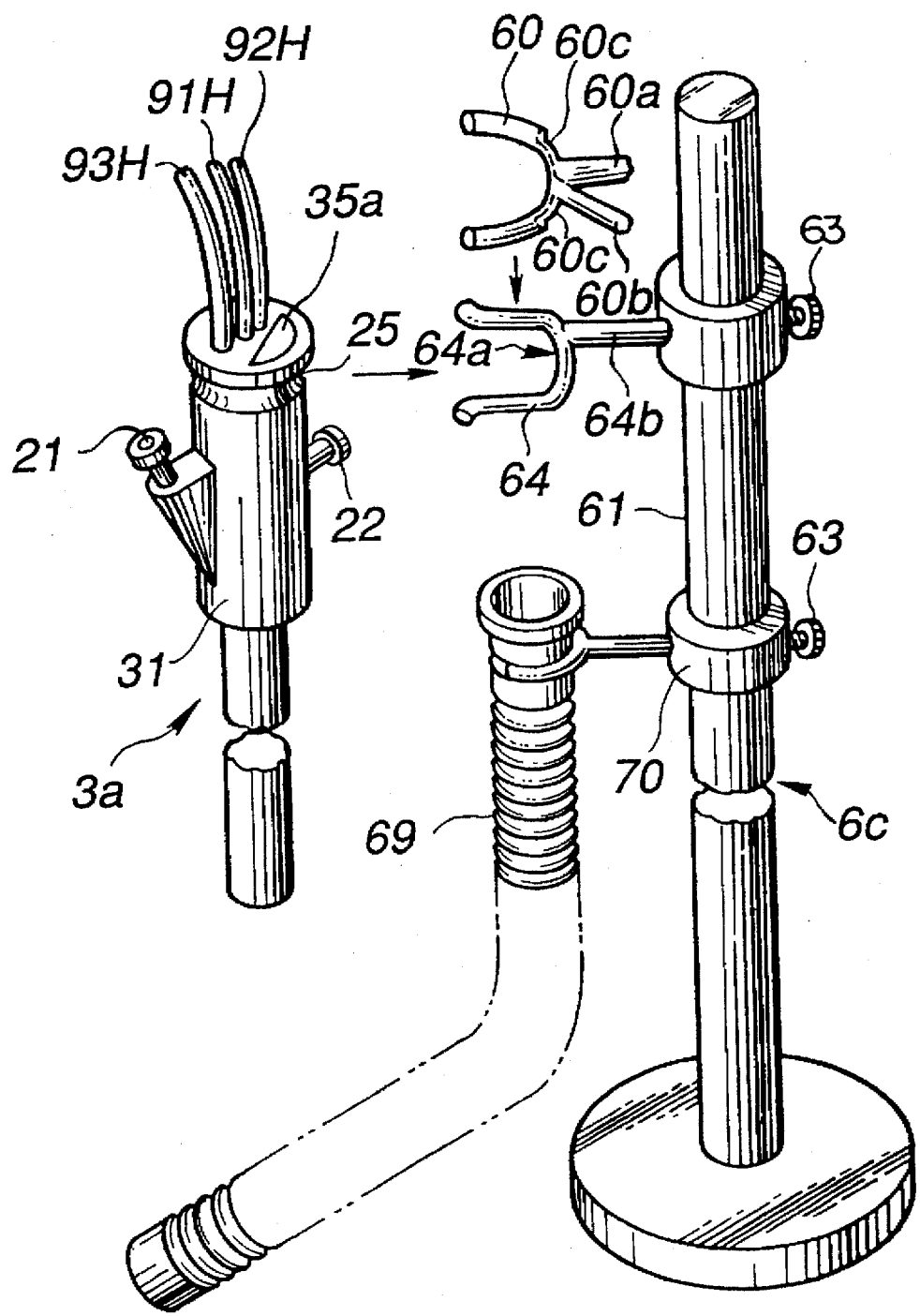

Therefore, in the cover holder 6c according to this embodiment, as shown in FIG. 24, a holding portion 70 in addition to the cover holding portion 61 is provided in the stand portion 61. The holding portion 70 comprises an inserting portion covering portion cover 69 made of cylindrical soft-type resin and having a length larger than that of the inserting portion covering portion having a longest effective length and having a diameter larger than that of the inserting portion covering portion 3a, and being adjustable in the vertical position and in the orientation in the same manner as the cover holding portion 61. The other compositions are the same as in the aforementioned third embodiment.

The operation of the cover holder 6c will now be described.

Firstly, in advance of attaching the inserting portion covering portion 3a to the cover holder 6c, the holding portion 64a of the cover holding member 64 being covered with the sterilized holding portion cover 60 is substantially accorded with the inserting opening of the inserting portion cover 69 provided in the holding portion 70.

Next, the distal end side of the inserting portion covering portion 3a is inserted into the opening portion of the inserting portion covering portion cover 69.

Then it is further inserted into a predetermined position of the inserting portion covering portion 69 to rest the cover holding member resting portion 25 on the cover holding member 64 of the cover holding portion 62, and the covering endoscope 4 is inserted.

In this manner, by providing the cover holder with the inserting portion covering portion cover, it is possible to prevent the inserting portion covering portion from being contaminated by touching the floor when the inserting portion covering portion having a long inserting length is rested on the cover holder.

Also, due to the inserting portion covering portion having a larger length than that of the inserting portion covering portion having the largest inserting length and having a diameter larger than that of the inserting portion covering portion having the largest inserting diameter, this embodiment can be applied to any kind of cover-type endoscope.

Moreover, since the inserting portion covering cover is formed of the soft-type resin, it is possible for the operator to touch the inserting portion covering portion thereover without contaminating it so as to enhance the efficiency of the attaching operation. The other operations and the advantages are the same as in the aforementioned embodiment.

Since the inserting portion covering portion cover 69 is formed of the soft-type resin and a helical groove is formed over the entire length to provide a desirable bending property and break-resistance in the central direction, the inserting portion covering portion 3a can be protected.

Further, if the inserting portion covering portion cover 69 is formed of transparent material, the position of the distal end of the inserting portion covering portion 3a can be easily viewed from outside.

Figure 25:
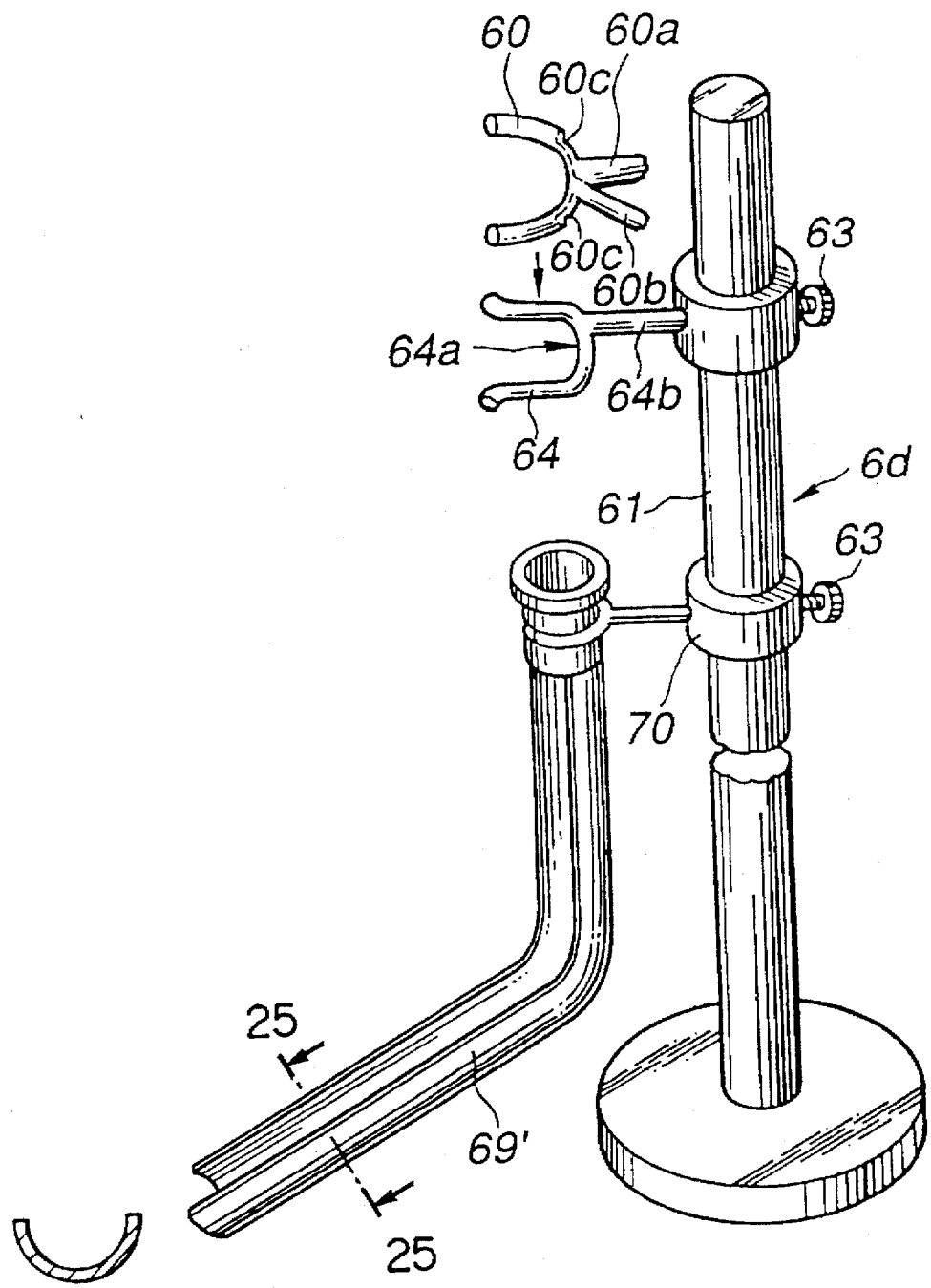

It is also possible to compose the inserting portion covering portion cover 69, not of cylindrical shape as shown in FIG. 25, but of a cover holder 6d provided with a semi-cylindrical inserting portion covering portion cover 69' formed to remain only at the part in contact with the floor.

Another example of the cover holding member will now be described with reference to FIGS. 26–30.

A cover holder 6e according to this embodiment is mounted on the inspection bed for reducing space.

Figure 26:
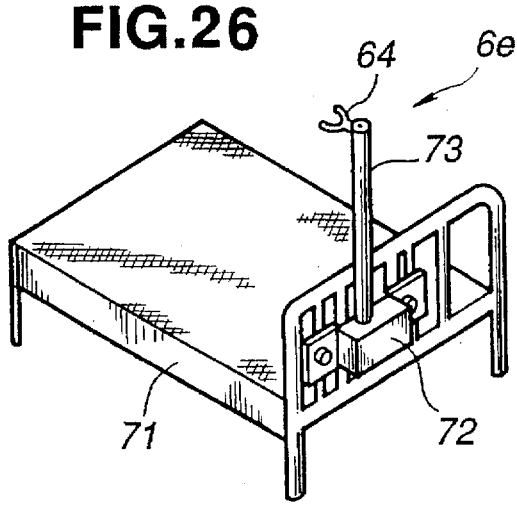
Figure 27:
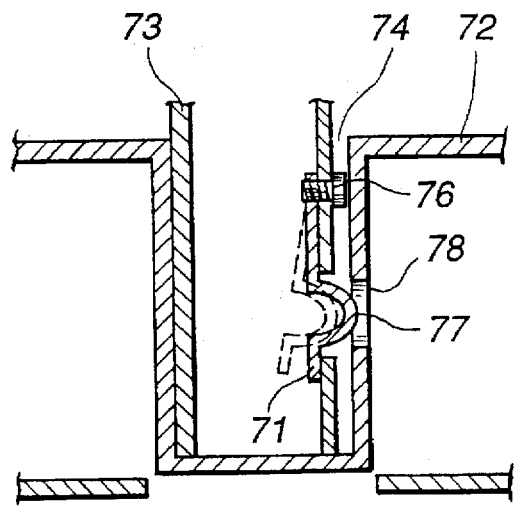

Namely, as shown in FIG. 26, an adaptor 72 for coupling the cover holder 6d is fixed to a head part of the inspection bed 71 through bolt and nut. The cover holder 6d is composed of a column 73 and a cover holding member 64. As shown in FIG. 27, the column 73 is inserted into and fixed to the fixing portion 74 of the adaptor 72. A stopper 77 is removably provided at the lower portion of the column 73 for preventing the adaptor 72 from fallen out. This stopper 77 is made of spring material and has an end fixed by a vis 76 and other end in released state. A convex portion 77 is formed in the middle portion acting for preventing the fallen out of the adaptor 72 by being inserted into and fixed to the fixing hole 78 of the adaptor 72 by its elastic deformation.

Figure 28:
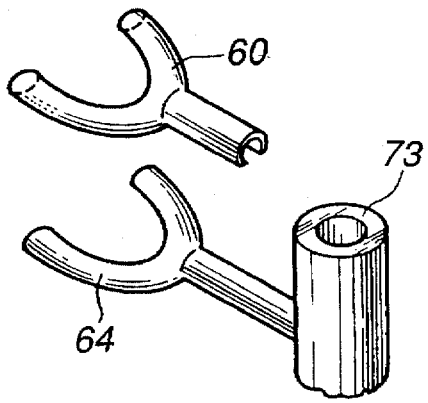

On the other hand, as shown in FIG. 28, the holding portion cover 60 can be removably attached to the cover holding member 64 of the cover holder 6d.

In this manner, by integrally mounting the cover holder with the inspection bed, the space for installing the cover holder becomes unnecessary.

Further, since the cover holder is fixed through the adaptor, this embodiment can be applied to any kind of inspection bed so as to become economical.

In addition, the cover holder would not disturb the moving operation of the inspection bed because of being removable therefrom.

Furthermore, since the stopper is provided on the column, the adaptor would not be fallen out from the column when the cover-type endoscope is removed from the cover holder so as to improve the operating efficiency.

Figures 29, 30:
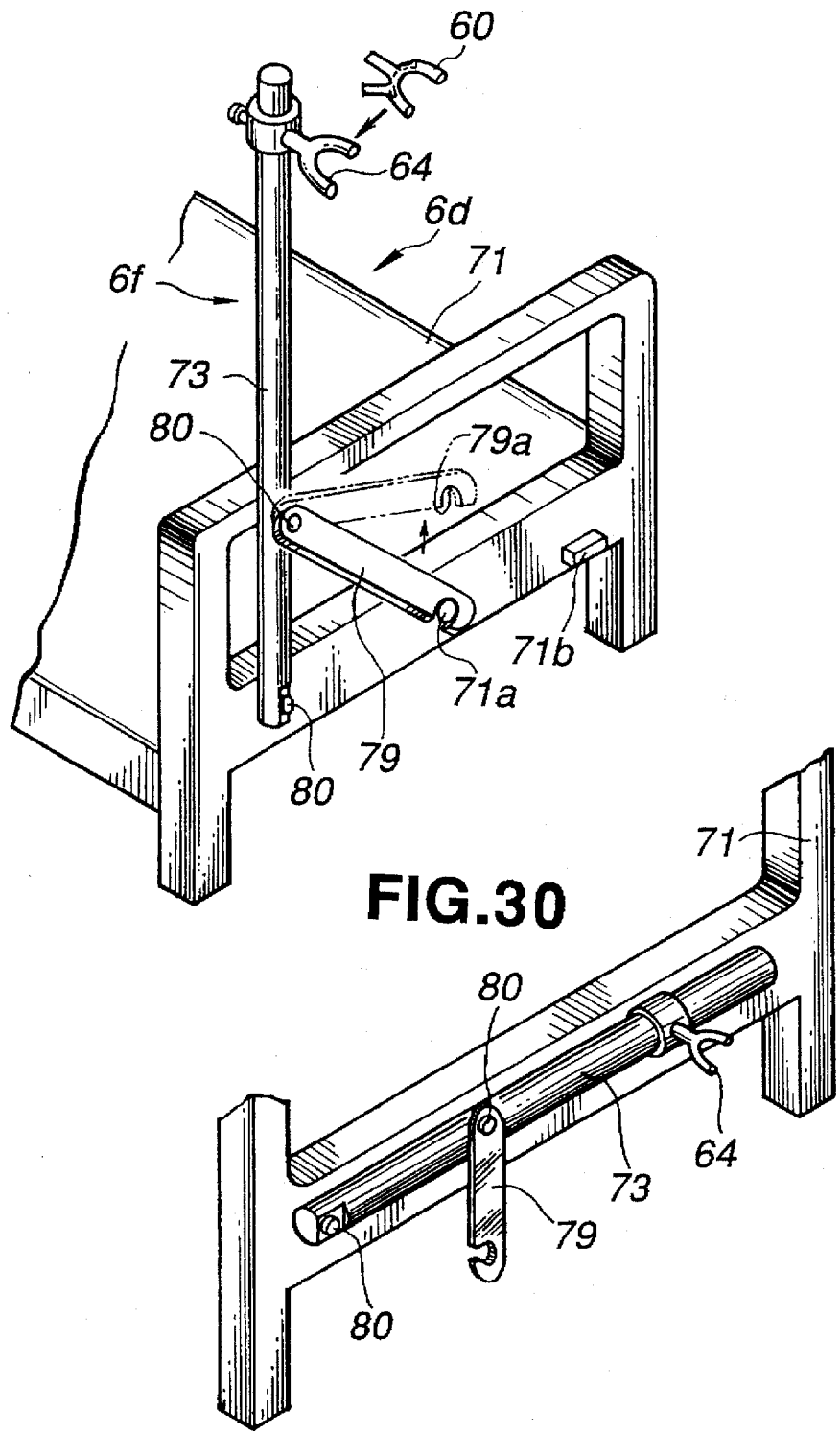

FIGS. 29 and 30 show another example of the inspection bed.

As shown in FIGS. 29 and 30, it is possible to fix the column 73 of the cover holder 6d to the inspection bed 71 through a link 79. At this time, the column 73 and the link 79 are rotatable by a joint pin 80. A fixing hole 79a is formed at the other end portion of the link 79 to be engaged with the fixing pin 71a provided in the inspection bed 71 so as to upright the column 73. Therefore, the cover holder 6d can be uprighted as required, and can be laid on its side by being disengaged from the link 79 when unnecessary. The other compositions, operations and advantages are the same as in the aforementioned sixth embodiment.

A fourth embodiment of the present invention will now be described with reference to FIGS. 31–33.

Figure 31:
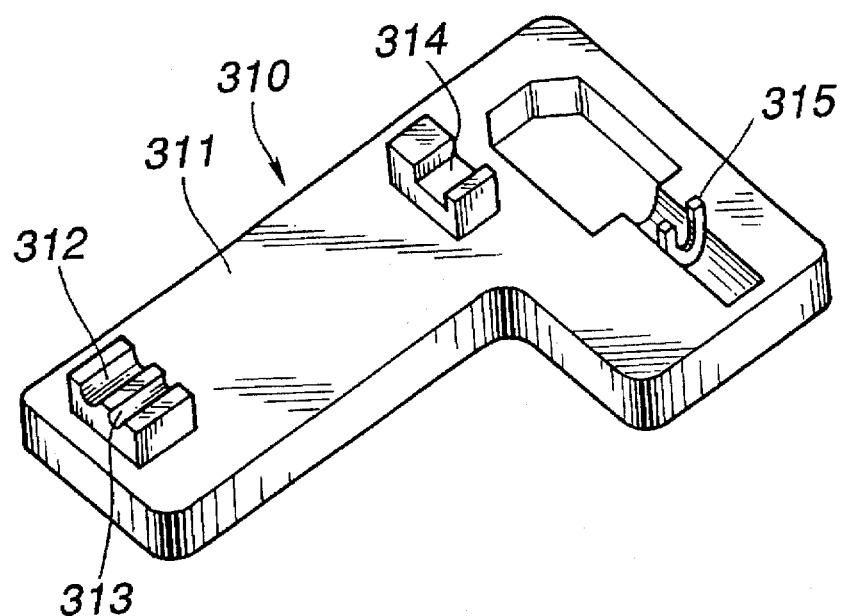

As shown in FIG. 31, an attaching tray 310 is composed of a substantially L-letter shaped tray 311, a universal cord fixing portion 312 for fixing the universal cord 46, a tube line fixing portion 313 for integrally fixing the hand-side water supply tube line 91H, the hand-side gas supply tube line 92H and the hand-side suction tube line 93H, a common fixing portion 314 for integrally fixing the universal cord 46 extending from the operating portion, the hand-side water supply tube line 91H, the hand-side gas supply tube line 92H and the hand-side suction tube line 93H, and a holding member 315 for holding the fixing mouth portion 31 of the inserting portion covering portion 3a, etc.

Figure 32:
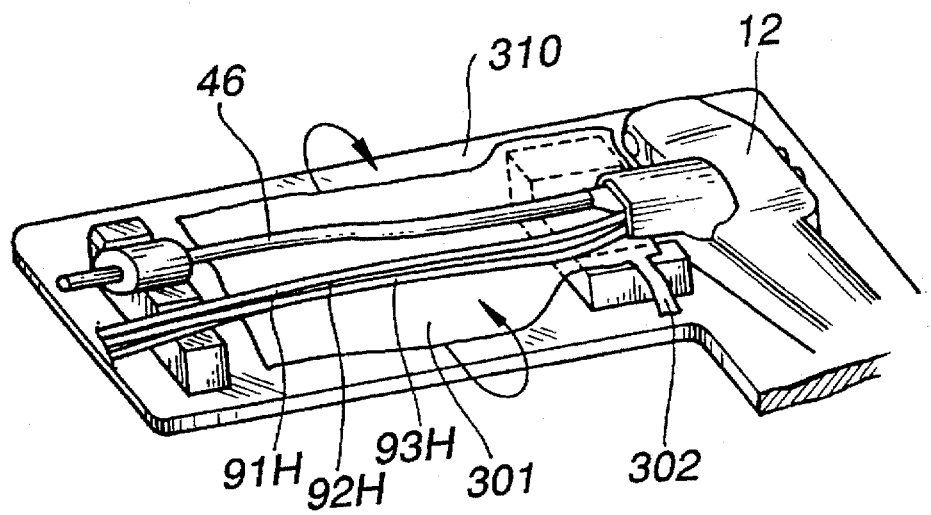
Figure 33:
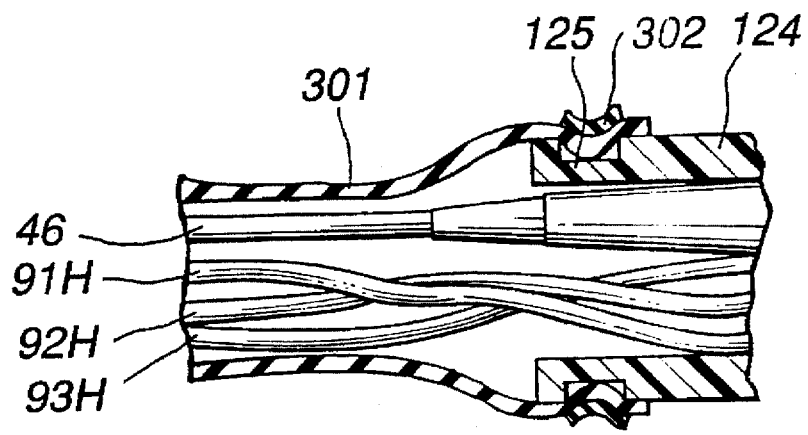

As shown in FIG. 32, the hand-side water supply tube line 91H, the hand-side gas supply tube line 92H, the hand-side suction tube line 93H and the universal cord 46 are fixed to a universal fixing portion 312, a tube line fixing portion 313 and a common fixing portion 314 respectively, and then a resin sheet 301 is set. Then, all the parts other than those being in contact with the universal fixing portion 312, the tube line fixing portion 313 and the common fixing portion 314 would become floated in the space portion, such that the end portion can be fixed by a binding member 302 or a tape 303 after the universal cord 46, the hand-side water supply tube line 91H, the hand-side gas supply tube line 92H and the hand-side suction tube line 93H are easily wound by the soft resin sheet in the direction shown by arrow.

Thus, since all the parts other than the fixing parts for fixing the tubes forming the tube lines to the universal cord becomes floated in the space, it is not necessary to manually grip the tubes and the universal cord when the resin sheet is attached, and the tubes would not be undesirably snagged when wound around the tube lines. As a result, the operation efficiency in attaching the resin sheet would be significantly enhanced.

A fifth embodiment of the present invention will now be described with reference to FIGS. 34–37.

In the cover-type endoscope apparatus, covers are frequently used. Therefore, it is necessary to establish an administrative system for these covers.

Figure 34:
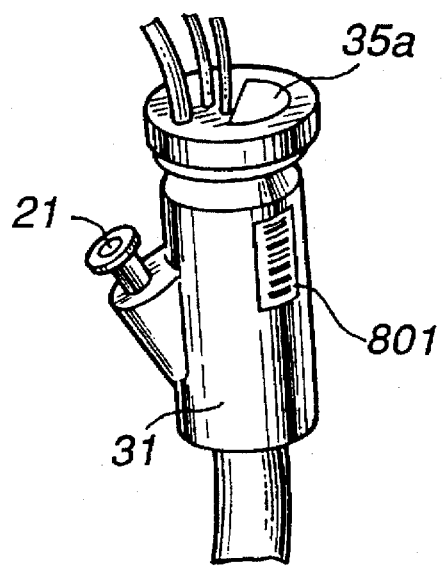
Figure 35:
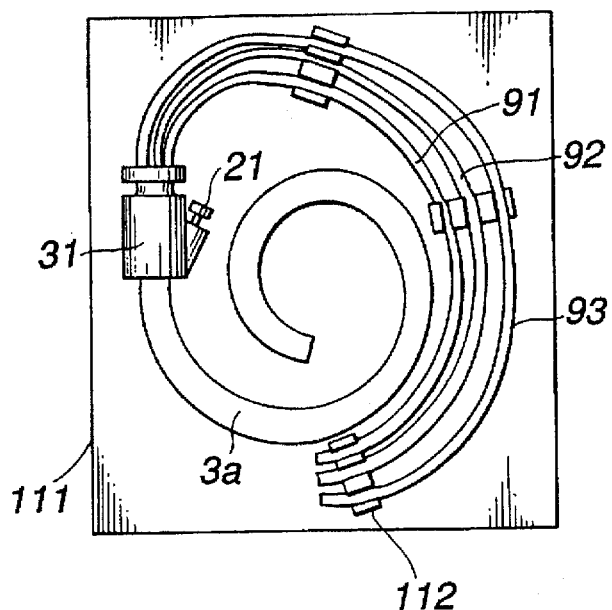
Figure 36:
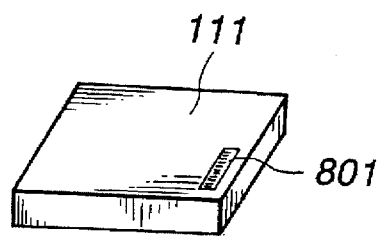

As shown in FIGS. 34–36, for example, a bar code seal 801 being capable of easily identified by an optical reader is attached in the production line to a package 111 of the inserting portion covering portion 3a and the endoscope cover for shipping.

Figure 37:
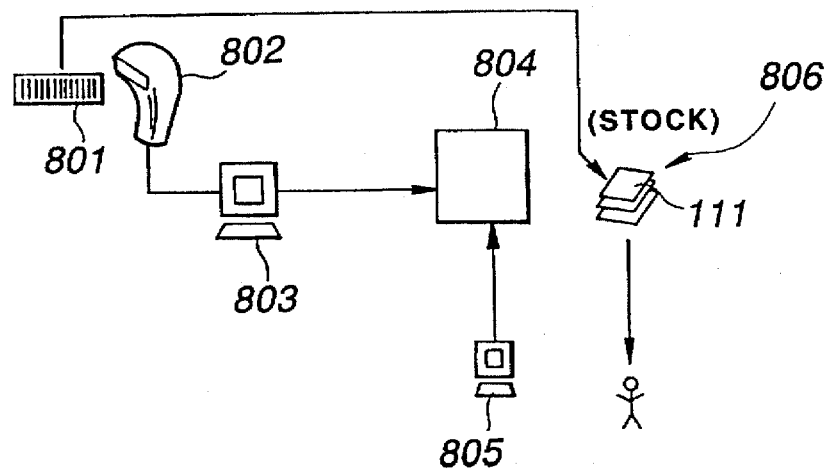

Namely, as shown in FIG. 37, each time a package 111 containing a sterilized cover for example is finished in the production line, the bar code seal 801 attached to the package 111 is read out by the optical reader 802 and the read out data are supplied to a central computer 804 through a production terminal 803. Upon receiving the data indicating the completion of the package 111, the central computer 804 corrects the number of stocks.

Further, order data are output to the central computer 804 through an order terminal 805. The central computer 804 then instantaneously examines the stocks and outputs proper data to a user 807, and the package 111 is transported to the user 807 from the stock storage place 806.

In this manner, by attaching the bar cord seal on the inserting portion covering portion, the assembling state and the progressing state of completed products in the production line can be securely read out by the optical reader, thereby accurately administering the processes.

Since the bar cord seal is attached also to the package, it is also possible to input/output stock/shipping administering data of products to the central computer through the optical reader so as to realize real-time stock administration.

According to the present invention, a variety of different embodiments over a wide range can be composed on the basis of the present invention without departing from the technical concept and the scope of the present invention. The present invention is not limited by any particular embodiment, but only by the following claims.

What is claimed is:

1. A cover-type endoscope apparatus comprising:
   a cover including a plurality of channels, wherein each said channel includes a flexible inserting-side tube line contained in an insert section of said cover and a flexible hand-side tube line located external to said inserting-side, said flexible inserting-side tube lines included in said channels being independent of one another;
   a covering endoscope in which an insert section is joined to an operation section and said operation section is joined to a universal cord, at least said operation section being covered with said cover; and
   a coupling means mounted directly to said operation section, including a plurality of coupling joint tubes, each of which is insertable into one of said inserting-side tube lines and one of said hand-side tube lines,
   wherein for at least one of said channels an inner diameter of said hand-side tube line is greater than an inner diameter of said corresponding inserting-side tube line, and
   wherein at least one of said coupling joint tubes has an inner diameter which is greater at a connection to said hand-side tube line than at a connection to said insertion-side tube line.

2. A cover-type endoscope apparatus according to claim 1, wherein said coupling means includes a means for preventing said coupled tube lines from coming off.

3. A cover-type endoscope apparatus according to claim 1, wherein said inserting-side tube line is formed of a multi-lumen tube.

4. A cover-type endoscope apparatus according to claim 1, wherein said cover is provided with an endoscope operation section fixing mouth portion at one end thereof for fixing the operation section of said covering endoscope, and said coupling means is mounted to said endoscope operation section fixing mouth portion.

5. A cover-type endoscope apparatus comprising:
   a covering endoscope in which an insert section is joined to an operation section and said operation section is joined to a universal cord;
   a cover including a plurality of channels covering at least said operation section, wherein each said channel includes a flexible inserting-side tube line contained in an insert section of said cover and a flexible hand-side tube line located external to said inserting-side, one end of said cover being provided with an operation section fixing mouth portion for fixing said operation section of said covering endoscope; and
   a coupling means mounted directly to said operation section fixing mouth portion, including a plurality of coupling joint tubes, each of which is insertable into one of said inserting-side tube lines and one of said hand-side tube lines,
   wherein for at least one of said channels an inner diameter of said hand-side tube line is greater than an inner diameter of said corresponding inserting-side tube line, and
   wherein at least one of said coupling joint tubes has an inner diameter which is greater at a connection to said hand-side tube line than at a connection to said insertion-side tube line.

6. A cover-type endoscope apparatus according to claim 5, wherein said coupling means includes a means for preventing said coupled tube lines from coming off.

7. A cover-type endoscope apparatus according to claim 5, wherein flexible inserting-side tube lines are independent of one another.

8. A cover-type endoscope apparatus comprising:
   a cover including a plurality of channels covering at least said operation section, wherein each said channel includes a flexible inserting-side tube line formed of a multi-lumen tube contained in an insert section of said cover and a flexible hand-side tube line located external to said inserting-side, said flexible inserting-side tube lines included in said channels being independent of one another;
   a covering endoscope in which an insert section is joined to an operation section and said operation section is joined to a universal cord, at least said operation section being covered with said cover; and
   a coupling means mounted directly to a fixing mouth portion of said operation section, including a plurality of coupling joint tubes, each of which is insertable into one of said inserting-side tube lines and one of said hand-side tube lines,
   wherein for at least one of said channels an inner diameter of said hand-side tube line is greater than an inner diameter of said corresponding inserting-side tube line, and
   wherein at least one of said coupling joint tubes has an inner diameter which is greater at a connection to said hand-side tube line than at a connection to said insertion-side tube line.

* * * * *